United States Patent
Lin

(10) Patent No.: US 10,556,878 B2
(45) Date of Patent: Feb. 11, 2020

(54) THIOUREA COMPOUNDS AND THEIR USE AS INHIBITORS OF SIRT2 OR SIRT5

(71) Applicant: CORNELL UNIVERSITY, Ithaca, NY (US)

(72) Inventor: Hening Lin, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 14/896,057

(22) PCT Filed: Jun. 6, 2014

(86) PCT No.: PCT/US2014/041251
§ 371 (c)(1),
(2) Date: Dec. 4, 2015

(87) PCT Pub. No.: WO2014/197775
PCT Pub. Date: Dec. 11, 2014

(65) Prior Publication Data
US 2016/0130246 A1    May 12, 2016

Related U.S. Application Data

(60) Provisional application No. 61/831,738, filed on Jun. 6, 2013.

(51) Int. Cl.
*C07D 335/06* (2006.01)
*C07C 335/08* (2006.01)

(52) U.S. Cl.
CPC ......... *C07D 335/06* (2013.01); *C07C 335/08* (2013.01)

(58) Field of Classification Search
CPC .................. C07D 335/06; C07C 335/05
(Continued)

(56) References Cited

U.S. PATENT DOCUMENTS 7,674,827 B2    3/2010    Kordes et al.

FOREIGN PATENT DOCUMENTS

WO    WO 2012/006391 A2    1/2012
WO    WO 2013/005727 A1    1/2013

OTHER PUBLICATIONS

Goodyer et al (Bioorg. Med. Chem. Lett., 2003; 13:3679-3680).*

(Continued)

*Primary Examiner* — Marcos L Sznaidman
*Assistant Examiner* — Rayna Rodriguez
(74) *Attorney, Agent, or Firm* — Scully Scott Murphy & Presser

(57) ABSTRACT

A compound useful as a Sirt2 or Sirt5 inhibitor having the formula (1) wherein: $R_1$ is a hydrocarbon group having at least two carbon atoms connected by carbon-carbon bonds, wherein said hydrocarbon group is optionally endcapped by a neutral or anionic oxygen-containing group; $R_{2a}$, $R_{2b}$, and $R_{2c}$ are independently selected from hydrogen atom and hydrocarbon groups; $X_0$, $X_1$, $X_2$, and $X_3$ are independently selected from —$(CH_2)_n$—, —$NR_5$—, —O—, —S—, and a bond, wherein n represents 1, 2, or 3, provided that at least one of $X_0$-$X_3$ is —$(CH_2)_n$—; and $R_3$ and $R_4$ are independently selected from the group consisting of hydrogen atom, hydrocarbon groups, biological groups, and protecting groups. Also described are pharmaceutical compositions of (Continued)

the inhibiting compounds, and methods of treatment by administration of the inhibiting compounds.

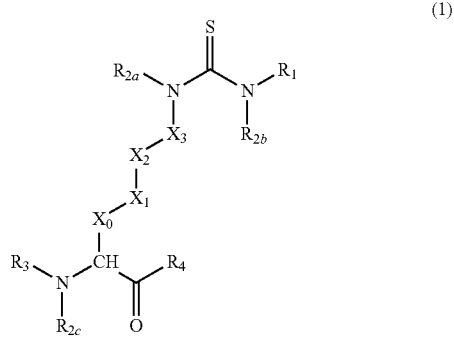

(1)

10 Claims, 5 Drawing Sheets

(58) Field of Classification Search
USPC .......................................................... 514/432
See application file for complete search history.

(56) References Cited

OTHER PUBLICATIONS

Huhtiniemi et al (Bioorg Med Chem, 2010; 18:5616-5625).*
Cen et al (Biochimica et Biophysica Acta, 2010; 1804:1635-1644).*
J. G. Cannon, Chapter Nineteen in Burger's Medicinal Chemistry and Drug Discovery, Fifth Edition, vol. I: Principles and Practice, Wiley-Interscience 1995, pp. 783-802.*
De Oliveira et al., "SIRT2 as a Therapeutic Target for Age-Related Disorders", *Experimental Pharmacology and Drug Discovery 3(82)*:1-9 (May 2012).
Du J. et al., "Sirt5 is a NAD-Dependent Protein Lysine Demalonylase and Desuccinylase", *Science 334*:806-809 (Nov. 11, 2011).
Haigis M.C. et al., "Mammalian Sirtuins: Biological Insights and Disease Relevance", *Annu. Rev. Pathol. Mech. Dis. 5*:253-295 (2010).

Heltweg B. et al., "Antitumor Activity of a Small-Molecule Inhibitor of Human Silent Information Regulator 2 Enzymes", *Cancer Research 66(8)*:4368-4377 (Apr. 15, 2006).
Huhtiniemi T. et al., "Oxadiazole-Carbonylaminothioureas as SIRT1 and SIRT2 Inhibitors", *Journal of Medicinal Chemistry 51(15)*:4377-4380 (2008).
Imai S-I et al., "Ten Years of NAD-Dependent SIR2 Family Deacetylases: Implications for Metabolic Diseases", *Trends in Pharmacological Sciences. 31(5)*:212-220 (2010).
Jiang W. et al., "Acetylation Regulates Gluconeogenesis by Promoting PEPCK1 Degradation Via Recruiting the UBR5 Ubiquitin Ligase", *Molecular Cell 43*:33-44 (Jul. 8, 2011).
Luthi-Carter R. et al., "SIRT2 Inhibition Achieves Neuroprotection by Decreasing Sterol Biosynthesis", *PNAS 107(17)*:7927-7932 (Apr. 27, 2010).
Michishita E. et al., "Evolutionarily Conserved and Nonconserved Cellular Localizations and Functions of Human SIRT Proteins", *Molecular Biology of the Cell 16*:4623-4635 (Oct. 2005).
Nakagawa T. et al., "SIRT5 Deacetylates Carbamoyl Phosphate Synthetase 1 and Regulates the Urea Cycle", *Cell 137*:560-570 (May 1, 2009).
North B.J. et al., "The Human Sir2 Ortholog, SIRT2, is an NAD+-Dependent Tubulin Deacetylase", *Molecular Cell 11*:437-444 (Feb. 2003).
Park J. et al., "SIRT5-Mediated Lysine Desuccinylation Impacts Diverse Metabolic Pathways", *Molecular Cell 50*:919-930 (Jun. 27, 2013).
Sauve A.A. et al., "The Biochemistry of Sirtuins", *Annu. Rev. Biochem. 75*:435-465 (2006).
Tsogoeva S.B. et al., "Asymmetric Organocatalysis with Novel Chiral Thiourea Derivatives: Bifunctional Catalysts for the Strecker and Nitro-Michael Reactions", *Eur. J. Org. Chem. 2005*:4995-5000 (2005).
Tsuji T. et al., "Synthetic Studies on β—Lactam Antibiotics. VII. Mild Removal of the Benzyl Ester Protecting Group With Aluminum Trichloride", *Tetrahedron Letters 30*:2793-2796 (1979).
Wang Y-K et al., "A Novel Electrochemical Membrane Bioreactor as a Potential Net Energy Producer for Sustainable Wastewater Treatment", *Scientific Reports 3*:1-6 (2013).
Zhang Y. et al., "Identification of a Small Molecule SIRT2 Inhibitor With Selective Tumor Cytotoxicity", *Biochemical and Biophysical Research Communications 386*:729-733 (2009).
International Search Report dated Oct. 8, 2014 received from International Application No. PCT/US2014/041251.

* cited by examiner

3A

3B

3C

THIOUREA COMPOUNDS AND THEIR USE AS INHIBITORS OF SIRT2 OR SIRT5

CROSS-REFERENCE TO RELATED APPLICATIONS

This application claims priority from U.S. Provisional Application No. 61/831,738, filed Jun. 6, 2013, which is herein incorporated by reference in its entirety.

STATEMENT REGARDING FEDERALLY SPONSORED RESEARCH

This invention was made with government support under Contract No. GM086703 and CA163255 awarded by the National Institutes of Health. The government has certain rights in the invention.

BACKGROUND OF THE DISCLOSURE

Sirtuins are a class of enzymes known as nicotinamide adenine dinucleotide (NAD)-dependent deacetylases. Humans have seven sirtuins, Sirt1-7, that regulate a variety of biological processes, including aging, transcription, and metabolism. Therefore, small molecules that can regulate sirtuin activity can be used to treat a host of diseases.

The process by which sirtuins catalyze NAD-dependent protein lysine deacetylation can be summarized by the process shown in FIG. 1. Sirtuins have been conserved through evolution and have been implicated in a number of biological functions, perhaps foremost being the regulation of lifespan (e.g., Haigis, M. C., et al., *Annu. Rev. Pathol.* 5, 253-295, 2010; and Imai, S.-i., et al., *Trends in Pharmacological Sciences* 31, 212-220, 2010).

Sirt2, in particular, is one of the seven members of the Sir2-family of NAD+-dependent deacetylases (or sirtuins) in humans. Among the seven mammalian sirtuins, Sirt2 is the only one that is mainly localized in the cytosol (e.g., Michishita, E., et al., *Mol. Biol. Cell* 16, 4623-4635, 2005). Two cytosolic Sirt2 substrates have been identified and confirmed in cellular studies, α-tubulin and phosphoenolpyruvate carboxykinase (PEPCK) (e.g., North, B. J., et al., *Mol. Cell* 11, 437-444, 2003; Jiang, W., et al., *Mol. Cell* 43, 33-44, 2011). Sirt2 destabilizes microtubules by deacetylating α-tubulin Lys40. By deacetylating PEPCK and regulating PEPCK stability, Sirt2 also regulates gluconeogenesis.

The anti-cancer effects of small-molecule inhibitors of Sirt2 have been described, e.g., Heltweg, B., et al., *Cancer Res.* 66, 4368-4377, 2006; Zhang, Y., et al., *Biochem. Biophys. Res. Commun.* 386, 729-733, 2009. However, the known inhibitors generally have higher than optimal $IC_{50}$ values against Sirt2, and also lack specificity against Sirt2. Moreover, attaining such specificity against Sirt2 could provide significant advantages for the treatment of particular types of cancer, such as breast cancer, and more particularly, triple negative breast cancer. Sirt2 has also been shown to be involved in neurodegenerative disease (e.g., Luthi-Carter, R., et al., *Proc. Natl. Acad. Sci. USA*, 107(17):7927-32, Apr. 27, 2010, and de Oliveira, R. M., et al., *Front Pharmacol.,* 3:82, 2012). Thus, such inhibitors against Sirt2 could also provide an improved treatment of neurodegenerative disease.

Sirt5 is a mitochondrial sirtuin with weak deacetylase activity. However, it has since been discovered that it instead has very efficient desuccinylase and demalonylase activity (Du J. et al., *Science*, 334, 806-809, 2011). In particular, Sirt5 regulates the succinylation of many proteins and regulates their activity (Park, J. et al., *Mol. Cell* 50, 919-930, 2013), thereby possibly impacting the etiology and/or progression of a variety of diseases or conditions. One of the major phenotypes of Sirt5 deletion is the decreased ability to remove ammonia via synthesis and secretion of urea (Nakagawa, T. et al., *Cell* 137, 560-570, 2009; Yu, J. et al. *Sci. Rep.* 3, 2013).

BRIEF SUMMARY OF THE DISCLOSURE

The instant disclosure describes novel sirtuin inhibitors having improved and even selective activity against human Sirt2 or Sirt5 protein. These inhibitors are useful in the treatment of, for example, cancer (for example, breast cancer), neurodegenerative disease, diabetes, obesity, cardiovascular disease, blood clotting disorders, or inflammation.

In particular embodiments, the inhibitors considered herein have the following chemical structure:

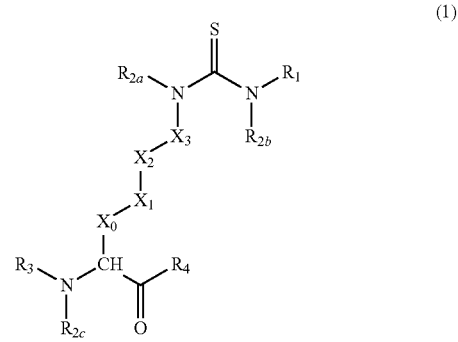

(1)

In Formula (1), $R_1$ is a hydrocarbon group having at least two carbon atoms connected by carbon-carbon bonds, wherein the hydrocarbon group optionally includes one heteroatom group selected from —O—, —$NR_5$—, and —S— that interrupts a carbon-carbon bond of the hydrocarbon group. One or more hydrogen atoms in the hydrocarbon group are optionally replaced with fluoro atoms, and the hydrocarbon group is optionally endcapped by a neutral or anionic oxygen-containing group. The groups $R_{2a}$, $R_{2b}$, and $R_{2c}$ are independently selected from hydrogen atom and hydrocarbon groups. The linking groups $X_0$, $X_1$, $X_2$, and $X_3$ are independently selected from —$(CH_2)_n$—, —$NR_5$—, —O—, —S—, and a bond, wherein n represents 1, 2, or 3, provided that at least one of $X_0$-$X_3$ is —$(CH_2)_n$—. The groups $R_3$ and $R_4$ are independently selected from the group consisting of hydrogen atom, hydrocarbon groups, amino acids, dipeptides, tripeptides, oligopeptides, proteins, nucleobases, nucleotides, dinucleotides, trinucleotides, oligonucleotides, monosaccharides, disaccharides, oligosaccharides, and protecting groups, wherein $R_4$ may optionally be selected from $OR_5$, $N(R_5)_2$, and $SR_5$; and $R_5$ is independently selected from hydrogen atom and hydrocarbon groups.

In particular embodiments of Formula (1), the inhibitor has the following formula:

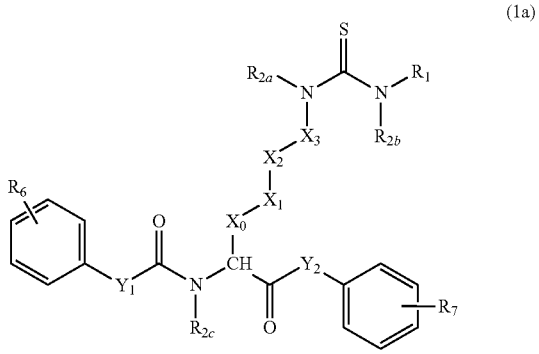

(1a)

In Formula (1a), $R_1$, $R_{2a}$, $R_{2b}$, $R_{2c}$, $X_0$, $X_1$, $X_2$, and $X_3$ are as defined above under Formula (1). The groups $R_6$ and $R_7$ are independently selected from hydrogen atom, unsubstituted hydrocarbon groups having up to six carbon atoms, and heteroatom-containing groups, such as halogen atom, hydroxy groups —OH, amine groups (e.g., —$NH_2$, —NHR, and —$NR_2$), alkoxy groups —OR, amide groups —N'C(O)R, amide groups —C(O)NR'R, keto groups —C(O)R, ester groups —C(O)OR, ester groups —OC(O)R, carbamate groups —OC(O)NR'R, carbamate groups —N(R')C(O)OR, urea groups —NR'C(O)NR, and sulfonyl groups (e.g., —$SO_2R$), wherein R is a hydrocarbon group having up to six carbon atoms, and R' is a hydrogen atom or a hydrocarbon group having up to six carbon atoms. The groups $Y_1$ and $Y_2$ are independently selected from —O—, —$NR_5$—, —S—, —$CH_2$—, —$CH_2O$—, —$CH_2NR_5$—, and —$CH_2S$—, groups.

In another aspect, the instant disclosure is directed to a method for treating a subject afflicted with a disorder treatable by inhibiting Sirt2 or Sirt5 activity. In the method, a subject afflicted with such a disorder, particularly cancer (e.g., breast cancer) or a neurodegenerative disorder (e.g., Parkinson's, Huntington's, or Alzheimer's) is administered at least one inhibiting compound selected from Formula (1) or (1a), described above, in a pharmaceutically effective amount for treating the disorder. In a first particular embodiment, a subject suffering from a Sirt2-related disorder, such as a neurodegenerative disorder or a cancer, or a Sirt5 disorder, is administered a pharmaceutically effective amount of an inhibiting compound according to Formula (1) or (1a), provided that the hydrocarbon group of $R_1$ is not endcapped by a neutral or anionic oxygen-containing group. In a second particular embodiment, a subject suffering from a Sirt5-related disorder, such as a cancer, neurodegenerative disease, diabetes, obesity, cardiovascular disease, blood clotting disorder, or inflammation, or a Sirt2 disorder, is administered a pharmaceutically effective amount of an inhibiting compound according to Formula (1) or (1a), provided that the hydrocarbon group of $R_1$ is endcapped by a neutral or anionic oxygen-containing group.

BRIEF DESCRIPTION OF THE FIGURES

FIG. 2A is the Western blot image showing that treating the cells with Compound I5-2e increased the succinylation level on proteins at 48 and 72 hours. FIG. 2B is the Coomassie blue stained protein gel showing that each sample contains roughly the same amount of proteins. The control sample was treated with DMSO and grown for 72 hours. All the cells grew for the same duration.

FIG. 3C is the structure of YC6-18e. FIG. 3A is the Western blot image showing that treating the cells with Compound YC6-18e increased the succinylation level on proteins at 24 and 48 hours. FIG. 3B is the Coomassie blue stained protein gel showing that each sample contains roughly the same amount of proteins (the last lane has less protein, but the succinylation level shown in A is actually higher than other lanes, suggesting that the level of succinylation is increased after 48 hours of treatment with Compound YC6-18e).

DETAILED DESCRIPTION OF THE DISCLOSURE

Figure 1:
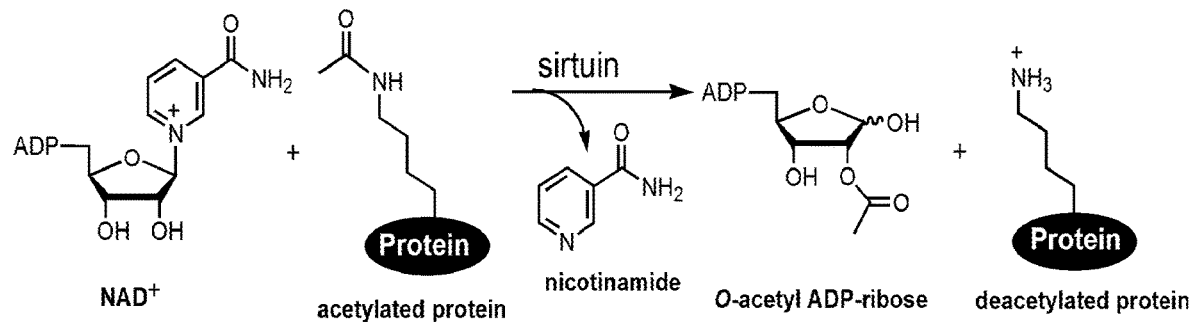
FIG. 1. General schematic showing the process by which sirtuins catalyze NAD-dependent protein lysine deacetylation.

For convenience, before further description of the present invention, certain terms employed in the specification, examples, and appended claims are described here. These definitions should be read in light of the entire disclosure and as would be understood by a person skilled in the art.

The terms "a" and "an" are used herein to refer to one or to more than one (i.e., to at least one) of the grammatical object of the article. By way of example, "an element" can mean one or more elements, unless otherwise specified.

The term "amino acid" is intended to embrace all molecules, whether natural or synthetic, that include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of the foregoing. In some embodiments, the term "amino acid" refers only to the twenty known essential amino acids, or a subset thereof, i.e., glycine (G), alanine (A), valine (V), leucine (L), isoleucine (I), cysteine (C), methionine (M), phenylalanine (F), tyrosine (Y), tryptophan (W), proline (P), serine (S), threonine (T), asparagine (N), glutamine (Q), aspartic acid (D), glutamic acid (E), histidine (H), lysine (K), and arginine (R). In some embodiments, one or more of any of the foregoing classes or specific types of amino acids are excluded.

The term "polypeptide", and the terms "protein" and "peptide", which are used interchangeably herein, refer to a polymer of amino acids. Exemplary polypeptides include gene products, naturally-occurring proteins, homologs, orthologs, paralogs, fragments, and other equivalents, variants, and analogs of the foregoing. They may include one or more types of any of the amino acid residues described above, or a modified form thereof, and typically include at least 10, 20, 30, 40, or 50, and up to 80, 100, 120, 150, 200, 300, 400, 500, or 1,000 amino acid residues. The term "oligopeptide", as used herein, generally refers to a chain of amino acid residues of at least 4, 5, or 6 and up to 8, 10, 15, or 20. The terms "dipeptide" and "tripeptide" refer, respectively, to two and three linked amino acid residues.

As used herein, the term "hydrocarbon group" (also denoted by the group R) is, in a first embodiment, composed solely of carbon and hydrogen. In different embodiments, one or more of the hydrocarbon groups or linkers can contain precisely, or a minimum of, or a maximum of, for example, one, two, three, four, five, six, seven, eight, nine, ten, eleven, twelve, thirteen, fourteen, fifteen, sixteen, seventeen, eighteen, nineteen, or twenty carbon atoms, or a number of carbon atoms within a particular range bounded by any two of the foregoing carbon numbers. Hydrocarbon groups or linkers in different compounds described herein, or in different positions of a compound, may possess the same or different number (or preferred range thereof) of carbon atoms in order to independently adjust or optimize the activity or other characteristics of the compound. The term "hydrocarbon linker", as used herein, is a linking group that may be derived by any of the hydrocarbon groups by including at least one additional linking point by removal of one or more hydrogen atoms from the group (e.g., a —CH$_2$CH$_2$— or >CHCH$_3$ linking group can be derived from an ethyl (—CH$_2$CH$_3$) group by removal of one of the hydrogen atoms of the ethyl group, either from an adjacent carbon atom or same carbon atom, respectively).

The hydrocarbon groups or linkers (R) can be, for example, saturated and straight-chained (i.e., straight-chained alkyl groups or alkylene linkers). Some examples of straight-chained alkyl groups (or alkylene linkers) include methyl (or methylene linker, i.e., —CH$_2$—, or methine linker), ethyl (or ethylene or dimethylene linker, i.e., —CH$_2$CH$_2$— linker), n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, and n-eicosyl groups (or their respective linker analogs).

The hydrocarbon groups or linkers (R) can alternatively be saturated and branched (i.e., branched alkyl groups or alkylene linkers). Some examples of branched alkyl groups include isopropyl (2-propyl), isobutyl (2-methylprop-1-yl), sec-butyl (2-butyl), t-butyl (1,1-dimethylethyl-1-yl), 2-pentyl, 3-pentyl, 2-methylbut-1-yl, isopentyl (3-methylbut-1-yl), 1,2-dimethylprop-1-yl, 1,1-dimethylprop-1-yl, neopentyl (2,2-dimethylprop-1-yl), 2-hexyl, 3-hexyl, 2-methylpent-1-yl, 3-methylpent-1-yl, isohexyl (4-methylpent-1-yl), 1,1-dimethylbut-1-yl, 1,2-dimethylbut-1-yl, 2,2-dimethylbut-1-yl, 2,3-dimethylbut-1-yl, 3,3-dimethylbut-1-yl, 1,1,2-trimethylprop-1-yl, and 1,2,2-trimethylprop-1-yl groups, isoheptyl, isooctyl, and the numerous other branched alkyl groups having up to 20 carbon atoms, wherein the "1-yl" suffix represents the point of attachment of the group. Some examples of branched alkylene linkers are those derived by removal of a hydrogen atom from one of the foregoing exemplary branched alkyl groups (e.g., isopropylene, —CH(CH$_3$)CH$_2$—).

The hydrocarbon groups or linkers (R) can alternatively be saturated and cyclic (i.e., cycloalkyl groups or cycloalkylene linkers). Some examples of cycloalkyl groups include cyclopropyl, cyclobutyl, cyclopentyl, cyclohexyl, cycloheptyl, and cyclooctyl groups. The cycloalkyl group can also be a polycyclic (e.g., bicyclic) group by either possessing a bond between two ring groups (e.g., dicyclohexyl) or a shared (i.e., fused) side (e.g., decalin and norbornane). Some examples of cycloalkylene linkers are those derived by removal of a hydrogen atom from one of the foregoing exemplary cycloalkyl groups.

The hydrocarbon groups or linkers (R) can alternatively be unsaturated and straight-chained (i.e., straight-chained olefinic or alkenyl groups or linkers). The unsaturation occurs by the presence of one or more carbon-carbon double bonds and/or one or more carbon-carbon triple bonds. Some examples of straight-chained olefinic groups include vinyl, propen-1-yl (allyl), 3-buten-1-yl (CH$_2$=CH—CH$_2$—CH$_2$—), 2-buten-1-yl (CH$_2$—CH=CH—CH$_2$—), butadienyl, 4-penten-1-yl, 3-penten-1-yl, 2-penten-1-yl, 2,4-pentadien-1-yl, 5-hexen-1-yl, 4-hexen-1-yl, 3-hexen-1-yl, 3,5-hexadien-1-yl, 1,3,5-hexatrien-1-yl, 6-hepten-1-yl, ethynyl, propargyl (2-propynyl), and the numerous other straight-chained alkenyl groups having up to 20 carbon atoms. Some examples of straight-chained olefinic linkers are those derived by removal of a hydrogen atom from one of the foregoing exemplary straight-chained olefinic groups (e.g., vinylene, —CH=CH—, or vinylidene).

The hydrocarbon groups or linkers (R) can alternatively be unsaturated and branched (i.e., branched olefinic or alkenyl groups or linkers). Some examples of branched olefinic groups include propen-2-yl (CH$_2$=C.—CH$_3$), 1-buten-2-yl (CH$_2$=C.—CH$_2$—CH$_3$), 1-buten-3-yl (CH$_2$=CH—CH.—CH$_3$), 1-propen-2-methyl-3-yl (CH$_2$=C(CH$_3$)—CH$_2$—), 1-penten-4-yl, 1-penten-3-yl, 1-penten-2-yl, 2-penten-2-yl, 2-penten-3-yl, 2-penten-4-yl, and 1,4-pentadien-3-yl, wherein the dot in any of the foregoing groups indicates a point of attachment. Some examples of branched olefinic linkers are those derived by removal of a hydrogen atom from one of the foregoing exemplary branched olefinic groups.

The hydrocarbon groups or linkers (R) can alternatively be unsaturated and cyclic (i.e., cycloalkenyl groups or cycloalkenylene linkers). The unsaturated and cyclic group can be aromatic or aliphatic. Some examples of unsaturated and cyclic hydrocarbon groups include cyclopropenyl, cyclobutenyl, cyclopentenyl, cyclopentadienyl, cyclohexenyl, cyclohexadienyl, phenyl, benzyl, cycloheptenyl, cycloheptadienyl, cyclooctenyl, cyclooctadienyl, and cyclooctatetraenyl groups. The unsaturated cyclic hydrocarbon group can also be a polycyclic group (such as a bicyclic or tricyclic polyaromatic group) by either possessing a bond between two of the ring groups (e.g., biphenyl) or a shared (i.e., fused) side, as in naphthalene, anthracene, phenanthrene, phenalene, or indene fused ring systems. Some examples of cycloalkenylene linkers are those derived by removal of a hydrogen atom from one of the foregoing exemplary cycloalkenyl groups (e.g., phenylene and biphenylene).

One or more of the hydrocarbon groups or linkers (R) may (i.e., optionally) be substituted with (i.e., include) one or more heteroatoms, which are non-carbon non-hydrogen atoms. Some examples of heteroatoms include oxygen (O), nitrogen (N), sulfur (S), and halogen (halide) atoms. Some examples of halogen atoms include fluorine, chlorine, bromine, and iodine. In some embodiments, the heteroatom atom inserts between at least two carbon atoms (as in —C—O—C— ether, —C—S—C— thioether, —C—N(R)—C— tertiary amine, or —C=N—C— imine) or between at least one carbon atom and at least one hydrogen atom (as in —C—OH, —C—SH, —C—NH$_2$, —C—NH—C—, or —C(=NH)C—), wherein the shown carbon atom in each case can be considered part of a hydrocarbon group R described above. In other embodiments, the heteroatom replaces one or more hydrogen atoms and/or one or more carbon atoms in the hydrocarbon group, as in halogen-substituted groups (e.g., a —$CH_2F$, —$CHF_2$, and —$CF_3$) and carbonyl-substituted groups, such as ketone and aldehyde groups. In some embodiments, the hydrocarbon is substituted with multiple oxygen atoms to result in a dialkyleneoxide or polyalkyleneoxide group, such as a diethyleneoxide or polyethyleneoxide group. In the case of nitrogen or sulfur substitution, the nitrogen or sulfur atom may be bonded to a sufficient number of groups to make it positively charged, as in an ammonium group (e.g., —$NR'_3{}^+$) or sulfonium group (e.g., —$SR'_2{}^+$), in which case the positively charged moiety is necessarily associated with a counteranion (wherein R' independently represents hydrogen atom or any of the hydrocarbon groups described above). Likewise, a heteroatom may bear a negative charge, as in a deprotonated carboxy, thiocarboxy, sulfonate, phosphonate, hydroxy, or thiol group, in which case the negatively charged moiety is necessarily associated with a countercation.

When two or more same or different heteroatoms are bound to each other or located on the same carbon atom, the resulting group containing the heteroatoms is herein referred to as a "heteroatom-containing group". Thus, substitution with one or more heteroatoms also includes heteroatom-containing groups, unless otherwise specified. Some examples of heteroatom-containing groups and linkers include carboxy (—C(O)OR' or —OC(O)R'), thiocarboxy (—C(S)OR' or —OC(S)R'), carboxamide (—C(O)$NR'_2$, —C(O)NR'—, or —N(R')C(O)—), urea (—NR'—C(O)—$NR'_2$ or —NR'—C(O)—NR'—), thiourea (—NR'—C(S)—$NR'_2$ or —NR'—C(S)—NR'—), carbamate (—NR'—C(O)—OR', —OC(O)—$NR'_2$, or —NR'—C(O)—O—), thiocarbamate (—NR'—C(S)—OR', —OC(S)—$NR'_2$, or —NR'—C(S)—O—), nitro ($NO_2$), nitrile (CN), sulfonyl (—$S(O)_2R'$ or —$S(O)_2$—), sulfinyl (i.e., sulfoxide, —S(O)R' or —S(O)—), disulfide (—C—S—S—C—), sulfonate (—$S(O)_2R'$), and amine oxide (as typically found in a nitrogen-containing ring), wherein R' independently represents hydrogen atom or any of the hydrocarbon groups (R) described above. For example, —C(O)OR' includes carboxylic acid (—C(O)OH) and carboxylic ester (—C(O)OR), where R is any of the hydrocarbon groups described above. The heteroatom-containing group may also either insert between carbon atoms or between a carbon atom and hydrogen atom, if applicable, or replace one or more hydrogen and/or carbon atoms.

In some embodiments, the hydrocarbon group or linker (R) is substituted with one or more halogen atoms to result in a partially halogenated or perhalogenated hydrocarbon group. Some examples of partially halogenated hydrocarbon groups include —$CHY_2$, —$CH_2Y$, —$CH_2CY_3$, —$CH(CY_3)_2$, or a halo-, dihalo-, trihalo-, or tetrahalo-substituted phenyl group, wherein Y represents any of F, Cl, Br, or I, and more commonly F or Cl. Some examples of perhalogenated hydrocarbon groups include —$CY_3$, —$CY_2CY_3$, —$CY_2CY_2CY_3$, —$CY(CY_3)_2$, or perhalophenyl, —$C_6Y_5$).

In particular embodiments, the hydrocarbon group (R) is, or includes, a cyclic or polycyclic (i.e., bicyclic, tricyclic, or higher cyclic) saturated or unsaturated (e.g., aliphatic or aromatic) hydrocarbon group that includes at least one ring heteroatom, such as one, two, three, four, or higher number of ring heteroatoms. Such heteroatom-substituted cyclic hydrocarbon groups are referred to herein as "heterocyclic groups". As used herein, a "ring heteroatom" is an atom other than carbon and hydrogen (typically, selected from nitrogen, oxygen, and sulfur) that is inserted into or replaces a ring carbon atom in a hydrocarbon ring structure. In some embodiments, the heterocyclic group is saturated. In other embodiments, the heterocyclic group is unsaturated, i.e., aliphatic or aromatic heterocyclic groups, wherein the aromatic heterocyclic group is also referred to herein as a "heteroaromatic ring", or a "heteroaromatic fused-ring system" in the case of at least two fused rings, at least one of which contains at least one ring heteroatom. The heterocyclic group may be bound via a ring carbon atom or ring heteroatom to the remainder of the sirtuin inhibiting compound, either directly or via any of the linking groups or atoms described herein.

Some examples of saturated heterocyclic groups containing at least one oxygen atom include oxetane, tetrahydrofuran, tetrahydropyran, 1,4-dioxane, 1,3-dioxane, and 1,3-dioxepane rings. Some examples of saturated heterocyclic groups containing at least one nitrogen atom include pyrrolidine, piperidine, piperazine, imidazolidine, azepane, and decahydroquinoline rings. Some examples of saturated heterocyclic groups containing at least one sulfur atom include tetrahydrothiophene, tetrahydrothiopyran, 1,4-dithiane, 1,3-dithiane, and 1,3-dithiolane rings. Some examples of saturated heterocyclic groups containing at least one oxygen atom and at least one nitrogen atom include morpholine and oxazolidine rings. An example of a saturated heterocyclic group containing at least one oxygen atom and at least one sulfur atom includes 1,4-thioxane. An example of a saturated heterocyclic group containing at least one nitrogen atom and at least one sulfur atom includes thiazolidine and thiamorpholine rings.

Some examples of unsaturated heterocyclic groups containing at least one oxygen atom include furan, pyran, 1,4-dioxin, benzofuran, dibenzofuran, and dibenzodioxin rings. Some examples of unsaturated heterocyclic groups containing at least one nitrogen atom include pyrrole, imidazole, pyrazole, pyridine, pyrazine, pyrimidine, 1,3,5-triazine, azepine, diazepine, indole, purine, benzimidazole, indazole, 2,2'-bipyridine, quinoline, isoquinoline, phenanthroline, 1,4,5,6-tetrahydropyrimidine, 1,2,3,6-tetrahydropyridine, 1,2,3,4-tetrahydroquinoline, quinoxaline, quinazoline, pyridazine, cinnoline, 5,6,7,8-tetrahydroquinoxaline, 1,8-naphthyridine, and 4-azabenzimidazole rings. Some examples of unsaturated heterocyclic groups containing at least one sulfur atom include thiophene, thianaphthene, benzothiophene, thiochroman, and thiochromene rings. Some examples of unsaturated heterocyclic groups containing at least one oxygen atom and at least one nitrogen atom include oxazole, isoxazole, benzoxazole, benzisoxazole, oxazoline, 1,2,5-oxadiazole (furazan), and 1,3,4-oxadiazole rings. Some examples of unsaturated heterocyclic groups containing at least one nitrogen atom and at least one sulfur atom include thiazole, isothiazole, benzothiazole, benzoisothiazole, thiazoline, and 1,3,4-thiadiazole rings.

In some embodiments, any of the generic substituents (e.g., R, $R_1$, $R_2$, and the like) described below may independently exclude any one or more of the classes, subclasses, or particular hydrocarbon groups described above, or may independently include only specific hydrocarbon groups selected from the hydrocarbon groups (R) described above.

In a first aspect, the instant disclosure is directed to compounds possessing Sirt2 or Sirt5 inhibitory behavior, wherein the compounds have the following structure:

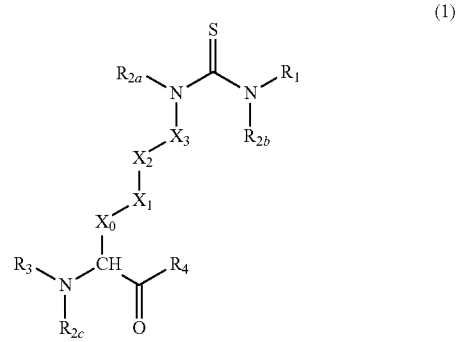

(1)

In Formula (1), the group $R_1$ is a hydrocarbon group (R) having at least two carbon atoms connected by carbon-carbon bonds. In different embodiments, the hydrocarbon group of $R_1$ may have precisely or at least two, three, four, five, six, seven, eight, nine, ten, eleven, twelve, thirteen, fourteen, fifteen, sixteen, seventeen, eighteen, nineteen, or twenty carbon atoms, or a number of carbon atoms within a range bounded by any two of the foregoing numbers of carbon atoms. In more particular embodiments, the hydrocarbon group of $R_1$ may have precisely or at least two, three, four, five, six, seven, eight, nine, ten, eleven, or twelve carbon atoms, and up to thirteen, fourteen, fifteen, sixteen, seventeen, eighteen, nineteen, or twenty carbon atoms. The hydrocarbon group may be composed of only carbon and hydrogen atoms, or may also include one heteroatom group selected from —O—, —$NR_5$—, and —S— that interrupts a carbon-carbon bond of the hydrocarbon group, wherein $R_5$ is a hydrogen atom or a hydrocarbon group (R). One or more hydrogen atoms in the hydrocarbon group of $R_1$ may be (i.e., optionally) replaced with fluoro atoms. In some embodiments, the hydrocarbon group of $R_1$ is a straight-chained or branched alkyl, alkenyl, or other aliphatic group having any number of carbon atoms provided above. In other embodiments, the hydrocarbon group of $R_1$ is a saturated or unsaturated (aliphatic or aromatic) cyclic group. In yet other embodiments, the hydrocarbon group of $R_1$ is an aromatic or heteroaromatic monocyclic or polycyclic group.

In one set of embodiments, the hydrocarbon group of $R_1$ is endcapped by at least one (i.e., one or more) oxygen-containing functional group that is either neutral (uncharged) or anionic (negatively charged). Some examples of such groups include hydroxy (—OH), alkoxy (—OR"), keto (—C(O)R"), carboxylate (—COO$^-$), carboxylic acid (—COOH), carboxylic acid ester (—C(O)OR" or —OC(O)R"), amide (—NR"C(O)R or —C(O)NR"R"), urea (—NR"C(O)NR"), carbamate (—OC(O)NR"R" or —N(R")C(O)OR"), thiocarboxylate (—CSO), sulfonate (—$SO_3^-$), sulfonic acid (—$SO_3H$), sulfonic acid ester (—$SO_3R$"), sulfone (—$SO_2R$"), sulfoxide (—S(O)R"), phosphonate (—$PO_3^{2-}$), phosphonic acid (e.g., —P(O)(OH)$_2$), phosphonate ester (—P(O)(OR")$_2$), and nitro (—$NO_2$) groups, wherein the foregoing R" group is independently selected from hydrogen atom and hydrocarbon groups having up to six, but more typically one, two, or three carbon atoms selected from any of the hydrocarbon groups R described above. When the hydrocarbon group of $R_1$ is endcapped by at least one oxygen-containing functional group, the resulting compound of Formula (1) is particularly considered herein as a Sirt5 inhibitor, although the indicated compound of Formula (1) may or may not alternatively or in addition inhibit Sirt2.

The term "endcapped", as used herein, generally indicates that the oxygen-containing functional group is located on a carbon atom most distal in terms of atom numbers (or atom lengths) from the connection point of the hydrocarbon group of $R_1$ to the thiourea nitrogen atom shown in Formula (1). The foregoing definition of the term "endcapped" particularly applies to $R^1$ hydrocarbon groups having up to four carbon atoms. For example, if $R_1$ is an n-propyl group endcapped by a hydroxy group, the resulting endcapped propyl group would correspond to —$CH_2CH_2CH_2OH$. If there are two or more equally most distal carbon atoms in the $R_1$ group, then the oxygen-containing functional group may be located on only one of the most distal carbon atoms, as in the case —$CH_2CH(CH_3)CH_2OH$, or alternatively, the two equally distal carbon atoms may each be functionalized by an oxygen-containing functional group, as in the case of —$CH_2CH(CH_2OH)_2$. In the event that $R_1$ is a hydrocarbon group having more than four carbon atoms (such as n-pentyl or n-hexyl), the term "endcapped" may or may not be less strictly defined by also including the possibility that the oxygen-containing functional group resides on a carbon atom second most distal or third most distal from the connection point of the hydrocarbon group of $R_1$ to the thiourea nitrogen atom shown in Formula (1). For example, if $R_1$ is an n-hexyl group endcapped by at least one hydroxy group, the resulting endcapped hexyl group may correspond to, for example, —$CH_2CH_2CH_2CH_2CH_2CH_2OH$, or —$CH_2CH_2CH_2CH_2CH(OH)CH_3$, or —$CH_2CH_2CH_2CH(OH)CH_2CH_3$, or —$CH_2CH_2CH_2CH_2CH(OH)CH_2OH$.

In the case of a carboxylic acid ester, the ester group (R") may alternatively be a protecting group, as well known in the art, such as a t-butyl ester group, benzyl ester group, S-t-butyl (—S—C(CH$_3$)$_3$) group, or silyl ester (e.g., —Si(CH$_3$)$_3$)) group. The ester group masks the negative charge on the carboxylate and thus can increase the cell permeability of the compounds. Inside the cells, the ester group can be hydrolyzed to release the negatively charged carboxylate, which can inhibit Sirt5. In some embodiments, when the hydrocarbon group of $R_1$ is endcapped by at least one oxygen-containing functional group, the remainder of $R_1$ is constructed of only carbon and hydrogen atoms, i.e., no heteroatoms are present, except that one or more fluoro atoms may or may not be present.

In another set of embodiments, the hydrocarbon group of $R_1$ is not endcapped by an oxygen-containing functional group. When the hydrocarbon group of $R_1$ is not endcapped by at least one oxygen-containing functional group, the resulting compound of Formula (1) is particularly considered herein as a Sirt2 inhibitor, although the indicated compound of Formula (1) may or may not alternatively or in addition inhibit Sirt5. In some embodiments, when the hydrocarbon group of $R_1$ is not endcapped by at least one oxygen-containing functional group, the hydrocarbon group of $R_1$ does not include an oxygen-containing functional group altogether, whether endcapped or interior. In some embodiments, when the hydrocarbon group of $R_1$ is not endcapped by at least one oxygen-containing functional group, the hydrocarbon group of $R_1$ is constructed of only carbon and hydrogen atoms, i.e., no heteroatoms are present, except that one or more fluoro atoms may or may not be present.

The groups $R_{2a}$, $R_{2b}$, and $R_{2c}$ in Formula (1) are independently selected from hydrogen atom and hydrocarbon groups. The hydrocarbon groups for $R_{2a}$, $R_{2b}$, and $R_{2c}$ can be any of the hydrocarbon groups provided above for R, R', and R", although more typically, the hydrocarbon groups for $R_{2a}$, $R_{2b}$, and $R_{2c}$ are lower alkyl groups containing one, two, three, or four carbon atoms, such as methyl, ethyl, n-propyl, isopropyl, n-butyl, sec-butyl, and isobutyl groups.

The linking groups $X_0$, $X_1$, $X_2$, and $X_3$ in Formula (1) are independently selected from —$(CH_2)_n$—, —$NR_5$—, —O—, —S—, and a bond, wherein $R_5$ is a hydrogen atom or any of the substituted or unsubstituted hydrocarbon groups R, R', or R" described above. The subscript n independently represents 1, 2, or 3. Following the rules of chemistry, the presence of a —$NR_5$—, —O—, or —S— linking group necessarily requires the aforesaid linking group to be connected on each side by a carbon atom. At least one of $X_0$-$X_3$ is a —$(CH_2)_n$— group. In some embodiments, at least two, three, or all of $X_0$-$X_3$ are —$(CH_2)_n$— groups. In particular embodiments, $X_0$, $X_1$, $X_2$, and $X_3$ are each selected from —$(CH_2)_n$—, wherein n is independently 1, 2 or 3, or wherein n is independently 1 or 2, or wherein n is 1 for each of $X_0$, $X_1$, $X_2$, and $X_3$.

The groups $R_3$ and $R_4$ in Formula (1) are independently hydrogen atom or any of the heteroatom-substituted or -unsubstituted hydrocarbon groups R described above, or a selection thereof, wherein $R_4$ may or may not alternatively be OH, $NH_2$, SH, OR, NHR, $NR_2$, or SR (i.e., $R_4$ may optionally be selected from —$OR_5$, —$N(R_5)_2$, and —$SR_5$, wherein $R_5$ is independently selected from hydrogen atom and hydrocarbon groups R, R', or R"). In some embodiments, one or both of $R_3$ and $R_4$ are non-biological (i.e. synthetic) groups containing at least 1, 2, 3, 4, or 5 and up to 10, 15, 20, 25, 30, 40, or 50 non-hydrogen atoms. In other embodiments, one or both of $R_3$ and $R_4$ are biologically related groups, such as an amino acid, dipeptide, tripeptide, oligopeptide (e.g., from 4 to 50 peptide units), polypeptide (e.g., protein, including an enzyme, antibody, or receptor), nucleobase, nucleoside, nucleotide, dinucleotide, oligonucleotide, polynucleotide, monosaccharide, disaccharide, oligosaccharide, or polysaccharide, any of which may be a small molecule, or a macromolecule containing hundreds of non-hydrogen atoms. In some embodiments, the polypeptide may be, for example, avidin, streptavidin, antibody or antibody fragment, or enzyme. In other embodiments, one or both of $R_3$ and $R_4$ are protecting groups. The protecting group can be any of the protecting groups described above, wherein a protecting group for $R_3$ is a protecting group appropriate for an amine group and $R_4$ is a protecting group appropriate for a carbonyl or carboxylic acid group. Some examples of amine protecting groups include carbobenzyloxy or benzyloxycarbonyl (Cbz), p-methoxybenzylcarbonyl, t-butyloxycarbonyl, acetyl, benzoyl, and tosyl groups. Some examples of carbonyl protecting groups include acetal and ketal groups, while some examples of protecting groups for carboxylic acid groups include methyl ester, benzyl ester, t-butyl ester, and silyl esters. In other embodiments, one or both of $R_3$ and $R_4$ are selected from saturated or unsaturated (i.e., aliphatic or aromatic) cyclic hydrocarbon groups, and more particularly, monocyclic or bicyclic aromatic or heteroaromatic groups, wherein the heteroaromatic group is typically bound to the structure in Formula (1) or (1a) via a ring carbon atom, which may be linked directly or via a linker group, such as any of the linking hydrocarbon groups described above, or via a heteroatom linking group, such as —NH—, —NR—, —O—, or —S—. In some embodiments, one or both of $R_3$ and $R_4$ contribute to the inhibition of Sirt2 or Sirt5 or provide an important function when the sirtuin inhibitory compound is administered to a subject. For example, $R_3$ and/or $R_4$ may make the inhibitory compound more bioavailable, function to target a receptor, function as an adjuvant drug moiety, or function as marker (e.g., a fluorophore) for a biodistribution study.

In particular embodiments of Formula (1), the inhibitory compound has the following formula:

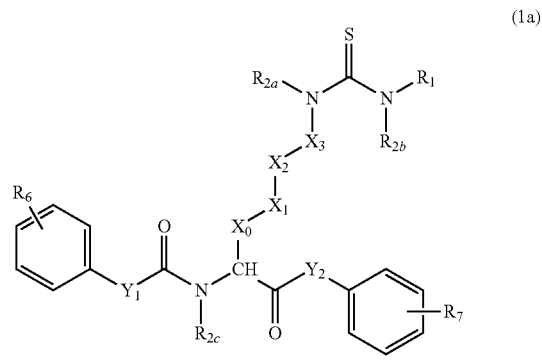

(1a)

In Formula (1a), $R_1$, $R_{2a}$, $R_{2b}$, $R_{2c}$, $X_0$, $X_1$, $X_2$, and $X_3$ in Formula (1a) are as defined in Formula (1) above. The groups $R_6$ and $R_7$ are independently selected from hydrogen atom, hydrocarbon groups having up to six carbon atoms, and heteroatom-containing groups. The hydrocarbon groups can be selected from those described under R, R', or R". The heteroatom-containing groups can be, for example, any of the oxygen-containing endcapping functional groups provided above for $R_1$, and other groups, such as amine (—$NH_2$, —NHR", or —NR"$_2$) or mercapto (—SH or —SR") groups. In some embodiments, the heteroatom-containing groups under $R_6$ and $R_7$ are independently selected from halogen atom, hydroxy groups —OH, amine groups (e.g., —$NH_2$, —NHR, and —$NR_2$), alkoxy groups —OR, amide groups —NR'C(O)R, amide groups —C(O)NR'R, keto groups —C(O)R, ester groups —C(O)OR, ester groups —OC(O)R, carbamate groups —OC(O)NR'R, carbamate groups —N(R')C(O)OR, urea groups —NR'C(O)NR, mercapto groups (—SH or —SR), and sulfonyl groups (e.g., —$SO_2$R), wherein R is a hydrocarbon group having up to six carbon atoms, and R' is a hydrogen atom or a hydrocarbon group having up to six carbon atoms. The groups $Y_1$ and $Y_2$ can be selected from any of the hydrocarbon linkers or heteroatom-containing linkers disclosed herein, or more particularly, independently selected from —O—, —$NR_5$—, —S—, —$CH_2$—, —$CH_2$O—, —$CH_2NR_5$—, and —$CH_2$S-groups.

Any of the Sirt2- or Sirt5-inhibiting compounds described herein can be made or modified to have improved properties for administration to a mammalian subject, e.g., to improve stability, cell penetrating ability, longer lifetime, and the like. For example, to enhance cell permeability of the substrate, the inhibiting compound can include a peptide chain containing a string of multiple amino acids, such as 8-10 arginine or chemically similar residues, or a polyalkyleneoxide chain, such as a polyethylene glycol (PEG) chain having 2, 3, 4, 5, 6, 7, 8, 9, 10, or a higher number of ethylene oxide units in any group other than $R_1$ (e.g., on the $R_{2a}$, $R_{2b}$, $R_{2c}$, $R_3$, $R_4$, $R_6$, or $R_7$ groups).

The sirtuin inhibiting compounds considered herein have the ability to partially or completely inhibit Sirt2 or Sirt5 activity. The ability of a sirtuin inhibiting compound to inhibit Sirt2 or Sirt5 activity is typically ascertained by measuring the $IC_{50}$ of the candidate compound. As used herein, "$IC_{50}$" or "50% half maximal inhibitory concentration" identifies how much of a compound is needed to inhibit activity by half. The $IC_{50}$ of a compound can be determined by constructing a dose-response curve and examining the effect of different concentrations of a compound on reducing or preventing enzymatic activity. $IC_{50}$ values can be calculated for a given inhibitor by determining the concentration needed to inhibit half of the maximum enzymatic activity. The mathematical analysis used for deriving an $IO_{50}$ value is well known in the art. The Sirt2 or Sirt5 inhibitors of the invention may inhibit Sirt2 or Sirt5 deacylase activity with an $IC_{50}$ of, for example, up to or less than 1 µM, 2 µM, 5 µM, 10 µM, 20 µM, 30 µM, 40 µM, 50 µM, or 100 or an $IC_{50}$ within a range bounded by any two of these values.

In some embodiments, the sirtuin inhibitor is a selective inhibitor of Sirt2 or Sirt5. A selective inhibitor of Sirt2 may exhibit an $IC_{50}$ value against Sirt2 that is lower than one or more (or all) other human sirtuins, such as Sirtuins 1, 3, 4, 5, and 6. Similarly, a selective inhibitor of Sirt5 may exhibit an $IC_{50}$ value against Sirt5 that is lower than one or more (or all) other human sirtuins, such as Sirtuins 1, 2, 3, 4, and 6. In some embodiments, the selective Sirt2 or Sirt5 inhibitor may exhibit an $IC_{50}$ of up to or less than 50, 40, 30, 20, 10, 5, 2, or 1 or as provided above, while the $IC_{50}$ of one or more (or all) other human sirtuins are greater than any of the foregoing values, or more particularly, greater than 50, 60, 70, 80, 90, or 100 µM. In one set of embodiments, an inihibitor compound of Formula (1) or (1a) with $R_1$ endcapped by at least one neutral or anionic oxygen-containing group is a selective inhibitor of Sirt2 or Sirt5, or an inhibitor of both Sirt2 and Sirt5. In another set of embodiments, an inhibitor compound of Formula (1) or (1a) with $R_1$ not endcapped by at least one neutral or anionic oxygen-containing group, or with $R_1$ not heteroatom-substituted or with $R_1$ composed of only carbon and hydrogen atoms (e.g., alkyl or alkenyl), is a selective inhibitor of Sirt2 or Sirt5, or an inhibitor of both Sirt2 and Sirt5.

The sirtuin inhibitory compounds described herein can be synthesized by methods well known in the art, as described in the Examples that follow. For example, a suitable precursor containing an amine group and functionalities shown in Formulas (1) or (1a), except for the thiourea moiety, can be reacted with an amide coupler (e.g., a diimide, such as DCC) in the presence of carbon disulfide ($CS_2$) to form an isothiocyanate analog thereof, and the isothiocyanate reacted with a suitably functionalized amine molecule having the desired $R_{2b}$ and $R_1$ groups to form a thiourea compound according to Formula (1) or (1a). The reaction conditions useful in accomplishing such a synthesis are well known in the art.

In another aspect, the invention is directed to a pharmaceutical composition that includes one or more of the sirtuin inhibiting compounds described above under Formula (1) or (1a) dispersed in one or more physiologically acceptable carriers or excipients. The phrase "pharmaceutically acceptable excipient" or "pharmaceutically acceptable carrier", as used herein, refers to a pharmaceutically acceptable material, composition or vehicle, such as a liquid or solid filler, diluent, carrier, manufacturing aid (e.g., lubricant, talc magnesium, calcium or zinc stearate, or stearic acid), solvent or encapsulating material, useful for carrying or transporting the therapeutic composition for administration to the subject. Each excipient should be "acceptable" in the sense of being compatible with the other ingredients of the formulation and physiologically safe to the subject.

The pharmaceutical composition can also include one or more stabilizers, surfactants, salts, buffering agents, additives, or a combination thereof. The stabilizer can be, for example, an oligosaccharide (e.g., sucrose, trehalose, lactose, or a dextran), a sugar alcohol (e.g., mannitol), or a combination thereof. The surfactant can be any suitable surfactant including, for example, those containing polyalkylene oxide units (e.g., Tween 20, Tween 80, Pluronic F-68), which are typically included in amounts of from about 0.001% (w/v) to about 10% (w/v). The salt or buffering agent can be any suitable salt or buffering agent, such as, for example, sodium chloride, or sodium or potassium phosphate, respectively. Some examples of additives include, for example, glycerol, benzyl alcohol, and 1,1,1-trichloro-2-methyl-2-propanol (e.g., chloretone or chlorobutanol). If required, the pH of the solutions can be suitably adjusted and buffered.

The pharmaceutical composition is useful in treating or preventing a disorder characterized by an excessive or otherwise abnormal or non-optimal Sirt2 or Sirt5 deacylase activity. The sirtuin inhibiting compound in the pharmaceutical composition can also be a physiologically acceptable salt or solvate of any of the modulator compounds described above. Acceptable salts and solvates can be made by any of the techniques known in the art. As known in the art, a salt can be produced by reacting a basic portion (e.g., amino) of the active compound with a Bronsted acid, such as HCl or $H_2SO_4$, or with an electrophile, such as $CH_3Br$. Alternatively, an anionic group may be located in $R_1$ or elsewhere in the molecule to result in a salt form of the compound. If desired, the initially introduced anion or cation can be exchanged with another anion or cation. As also known in the art, a solvate can be produced by dissolving or otherwise treating the active compound with a solvent under conditions where one, two, or more solvent molecules remain associated with each molecule of the active ingredient.

Pharmaceutical compositions (including cosmetic preparations) may comprise from about 0.00001 to 100%, such as from 0.001 to 10% or from 0.1% to 5% by weight of one or more of the sirtuin inhibiting compounds described herein. In certain topical formulations, the active agent is present in an amount in the range of approximately 0.25 wt. % to 75 wt. % of the formulation, or in the range of approximately 0.25 wt. % to 30 wt. % of the formulation, or in the range of approximately 0.5 wt. % to 15 wt. % of the formulation, or in the range of approximately 1.0 wt. % to 10 wt. % of the formulation.

In another aspect, the invention is directed to methods for treating or preventing a disorder (i.e., disease or condition) whose etiology or expression is dependent on Sirt2 or Sirt5 deacylase activity. The subject being treated is typically a human, although other mammals could possibly benefit. The disorder particularly considered herein is characterized by an excessive or otherwise non-optimal or abnormal level of Sirt2 or Sirt5 deacylase activity. The methods include administering to a subject a sirtuin inhibiting compound in a pharmaceutically effective amount, i.e., an amount that sufficiently inhibits Sirt2 or Sirt5 activity to result in an effective treatment or prevention of the disorder. As used herein, the term "inhibitor" is a substance that sufficiently reduces or completely inhibits Sirt2 or Sirt5 deacylase activity.

In one embodiment, the disease or condition being treated with the sirtuin inhibitor is a neurodegenerative disease. The term "neurodegenerative disease", as used herein, generally refers to a disease that manifests as the progressive loss of neuronal function and structure. The neurodegenerative disease can be, for example, Parkinson's, Alzheimer's, or Huntington's Disease, amyotrophic lateral sclerosis (ALS), peripheral neuropathies, and other conditions characterized by damage, necrosis or loss of neurons, including for example central, peripheral, or motor neurons. The role of Sirt2 in neurodegenerative disease is well known, e.g., Luthi-Carter, R., et al., *Proc. Natl. Acad. Sci. USA*, 107(17): 7927-32, Apr. 27, 2010, and de Oliveira, R. M., et al., *Front Pharmacol.*, 3:82, 2012. In particular embodiments, a Sirt2 inhibiting compound is administered for treating the neurodegenerative disease. In other embodiments, a Sirt5 inhibiting compound, or combination of Sirt2 and Sirt5 inhibitors, is administered for treating the neurodegenerative disease.

In another embodiment, the disease or condition being treated with the sirtuin inhibitor is cancer, which may be in the form of a neoplasm. The cancer can be located in any part of the body. Some examples of applicable body parts containing cancer cells include the breasts, lungs, stomach, intestines, prostate, ovaries, cervix, pancreas, kidney, liver, skin, lymphs, bones, bladder, uterus, colon, rectum, or brain. The cancer can also include the presence of one or more carcinomas, sarcomas, lymphomas, blastomas, or teratomas (germ cell tumors). The cancer may also be a form of leukemia. In some embodiments, the cancer is a triple negative breast cancer. The anti-cancer effects of small-molecule inhibitors of Sirt2 have been described, e.g., Heltweg, B., et al., *Cancer Res.* 66, 4368-4377, 2006; Zhang, Y., et al., *Biochem. Biophys. Res. Commun.* 386, 729-733, 2009. In particular embodiments, a Sirt2 inhibiting compound is administered for treating the cancer. In other embodiments, a Sirt5 inhibiting compound, or combination of Sirt2 and Sirt5 inhibitors, is administered for treating the cancer.

In yet other embodiments, the disease or condition being treated with the sirtuin inhibitor is diabetes, obesity, cardiovascular disease (e.g., atherosclerosis), a blood clotting disorder, or an inflammatory disorder or condition (e.g., rheumatoid arthritis). The diabetes can be, for example, a type 1 or 2 diabetes, pre-diabetes, or a related or at-risk condition, such as hypoglycemia. In some embodiments, the sirtuin inhibitor functions to normalize or maintain blood sugar level or insulin level or function. In other embodiments, the sirtuin inhibitor functions to treat or prevent a diabetic complication, such as renal failure, cardiovascular disease, retinopathy, neuropathy, ketoacidosis, or fatty liver disease.

The data obtained from cell culture assays and animal studies can be used in formulating a range of dosage for use in humans. The dosage of such compounds may lie within a range of circulating concentrations that include the $IC_{50}$ with little or no toxicity. The dosage may vary within this range depending upon the dosage form employed and the route of administration utilized. For any compound, the therapeutically effective dose can be estimated initially from cell culture assays. A dose may be formulated in animal models to achieve a circulating plasma concentration range that includes the $IC_{50}$ as determined in cell culture. Such information can be used to more accurately determine useful doses in humans. Levels in plasma may be measured, for example, by high performance liquid chromatography.

As is well known in the art, the dosage of the active ingredient(s) generally further depends on the disorder or condition being treated, the extent of the disorder or condition, the method of administration, size of the patient, and potential side effects. In different embodiments, depending on these and other factors, a suitable dosage of the Sirt2 or Sirt5 inhibitor and/or other active ingredient may be precisely, at least, above, up to, or less than, for example, 1 mg, 10 mg, 50 mg, 100 mg, 200 mg, 300 mg, 400 mg, 500 mg, 600 mg, 700 mg, 800 mg, 900 mg, 1000 mg, 1200 mg, or 1500 mg, or a dosage within a range bounded by any of the foregoing exemplary dosages. Furthermore, the composition can be administered in the indicated amount by any suitable schedule, e.g., once, twice, or three times a day or on alternate days for a total treatment time of one, two, three, four, or five days, or one, two, three, or four weeks, or one, two, three, four, five, or six months, or within a time frame therebetween. Alternatively, or in addition, the composition can be administered until a desired change in the disorder or condition is realized, or when a preventative effect is believed to be provided.

In certain embodiments, the sirtuin inhibiting compound described herein may be taken alone, while in other embodiments it may be taken in combination with one or more other compounds that may or may not also function to modulate Sirt2 or Sirt5 or favorably augment or modify the activity of the Sirt2- or Sirt5-inhibiting compound. In one embodiment, a mixture of two or more Sirt2- and/or Sirt5-inhibiting compounds may be administered to a subject in need thereof. In another embodiment, one or more Sirt2- and/or Sirt5-inhibiting compounds may be administered with one or more therapeutic agents for the treatment or prevention of a disorder whose etiology or expression is dependent, at least to some extent, on Sirt2 or Sirt5 deacylase activity. In some embodiments, the one or more therapeutic agents are administered at the same time as the Sirt2- or Sirt5-inhibiting compound (e.g., as a pharmaceutical composition containing the one or more therapeutic agents and Sirt2- and/or Sirt5 inhibiting compound), while in another embodiment, the one or more therapeutic agents are administered separately from the Sirt2-modulating compound. When using separate formulations, the Sirt2- or Sirt5-inhibiting compound may be administered at the same time, prior to, subsequent to, or intermittently or staggered with the administration of another therapeutic agent.

The Sirt2- or Sirt5-inhibiting compounds and their physiologically acceptable salts and solvates may be administered (and suitably formulated therefore) by, for example, injection (e.g. SubQ, IM, IP, IV), inhalation or insufflation (either through the mouth or the nose) or oral, buccal, sublingual, transdermal, nasal, parenteral or rectal administration. In some embodiments, a sirtuin inhibiting compound may be administered locally, at the site where the target cells are present, i.e., in a specific tissue, organ, or fluid (e.g., blood, cerebrospinal fluid, etc.). Sirtuin inhibiting compounds can be formulated for a variety of modes of administration, including systemic, topical, or localized administration. Techniques of administration and the design of formulations are well known in the art, such as described in, for example, Remington's Pharmaceutical Sciences, Meade Publishing Co., Easton, Pa.

Toxicity and therapeutic efficacy of sirtuin inhibiting compounds can be determined by standard pharmaceutical procedures in cell cultures or experimental animals. The $LD_{50}$ is the dose lethal to 50% of the population. The dose ratio between toxic and therapeutic effects ($LD_{50}/ED_{50}$) is the therapeutic index. Sirtuin inhibiting compounds that exhibit large therapeutic indexes are preferred. While sirtuin inhibiting compounds that exhibit toxic side effects may be used, it may be preferable to use a delivery system that targets such compounds to the site of affected tissue in order to minimize potential damage to uninfected cells and, thereby, reduce side effects.

Examples have been set forth below for the purpose of illustration and to describe the best mode of the invention at the present time. However, the scope of this invention is not to be in any way limited by the examples set forth herein.

EXAMPLE 1
Synthesis and Investigation of Initial Sirt2 and Sirt5 Inhibitors
Two initial compounds (Compounds 5 and 6) were synthesized and investigated for their sirtuin inhibiting abilities. The synthesis of these compounds is provided in the following scheme:
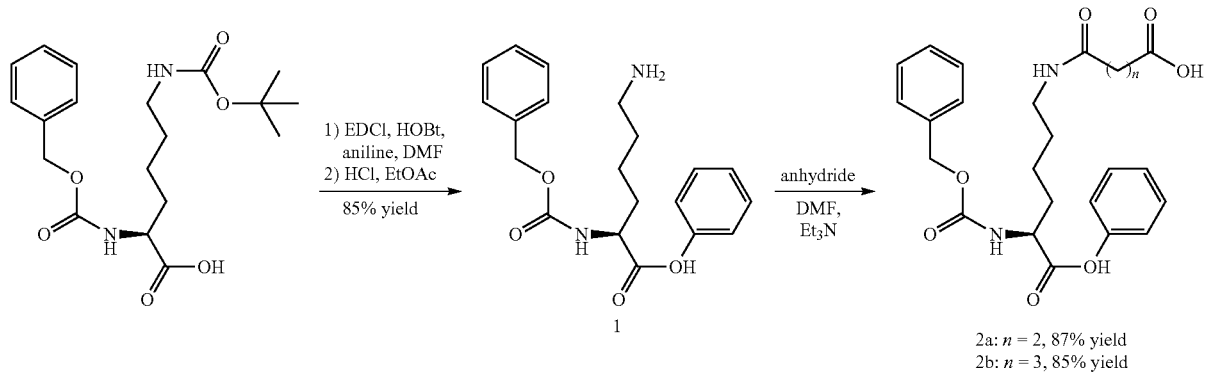
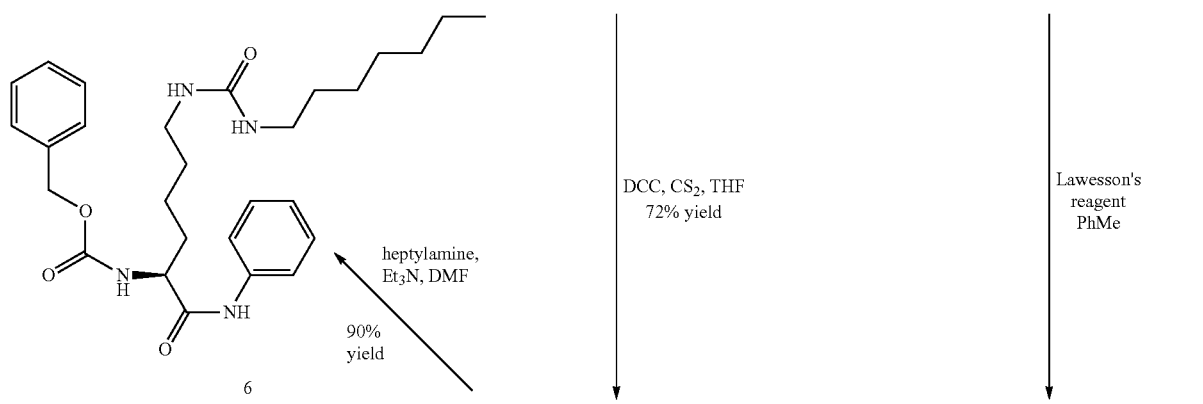
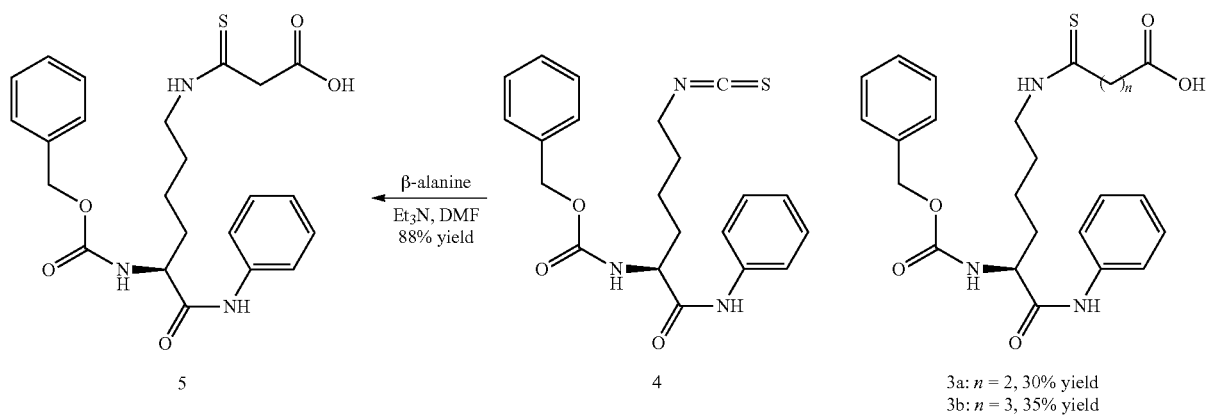

The synthesis of Compounds 5 and 6 began with the conversion of commercially available Cbz-Lys(Boc)-OH to compound 1 in two steps. Compound 1 was then reacted with dicyclohexylcarbodiimide (DCC) and $CS_2$ in dichloromethane to give the isothiocyanate Compound 4 (S. B. Tsogoeva, et al., *Eur. J. Org. Chem.*, vol. 2005, pp. 4995-5000, 2005). The thiourea Compound 5 was obtained by reacting Compound 4 with β-alanine and triethylamine. The thiourea compound 6 was obtained by reacting compound 4 with n-heptylamine and triethylamine.

The compounds were then tested for their sirtuin-inhibiting abilities. The $IC_{50}$ results are provided in Table 1 below.

TABLE 1

$IC_{50}$ values of compounds for different sirtuins

| | $IC_{50}$ (μM) | | | |
|---|---|---|---|---|
| Compound | Sirt1 | Sirt2 | Sirt3 | Sirt5 |
| 3a | NI[a] | NI[a] | NI[a] | >500[b] |
| 3b | NI[a] | NI[a] | NI[a] | 43 |
| 5 | NI[a] | NI[a] | NI[a] | 12 |
| 6 | 64 | 0.2 | NI[a] | NI[a] |

[a]NI, no inhibition at 256 μM.
[b]20% inhibition at 500 μM.

The results in Table 1 show that Compound 5 can inhibit the Sirt5-catalyzed desuccinylation reaction with an $IC_{50}$ value of 12 μM, which is 3.5 fold more potent than the corresponding thioglutaryl lysine Compound 3b. Furthermore, Compound 5 is also Sirt5-selective as it does not inhibit Sirt1, Sirt2, or Sirt3 even at 256 μM (Table 1).

To further confirm that the thiourea compound 5 is a mechanism-based inhibitor, the reaction mixture was analyzed by liquid chromatography-mass spectrometry (LC-MS). An ion with m/z of 1028.17 (corresponding to Compound 7a or protonated Compound 7b or 7c) was detected only when Compound 5 was incubated with both Sirt5 and NAD for 15 minutes, but not in negative controls without Sirt5 or NAD. In addition to Compound 7a or protonated Compound 7b or 7c, two new ions with m/z of 356.33 (corresponding to Compound 1) and 471.42 (corresponding to Compound 10) were also observed when Compound 5 was incubated with both Sirt5 and NAD, but not in negative controls without Sirt5 or NAD. Both Compounds 1 and 10 can be derived from the regular Sirt5-catalyzed deacylation reaction of Compound 7a (herein denoted as pathway A, as discussed in A. A. Sauve, et al., *Annu. Rev. Biochem.*, 75, 435-465, 2006) or by an alternative hydrolysis pathway of 7a that is different from the regular sirtuin-catalyzed deacylation pathway (herein denoted as pathway B). The two possible pathways (A and B) are shown below:

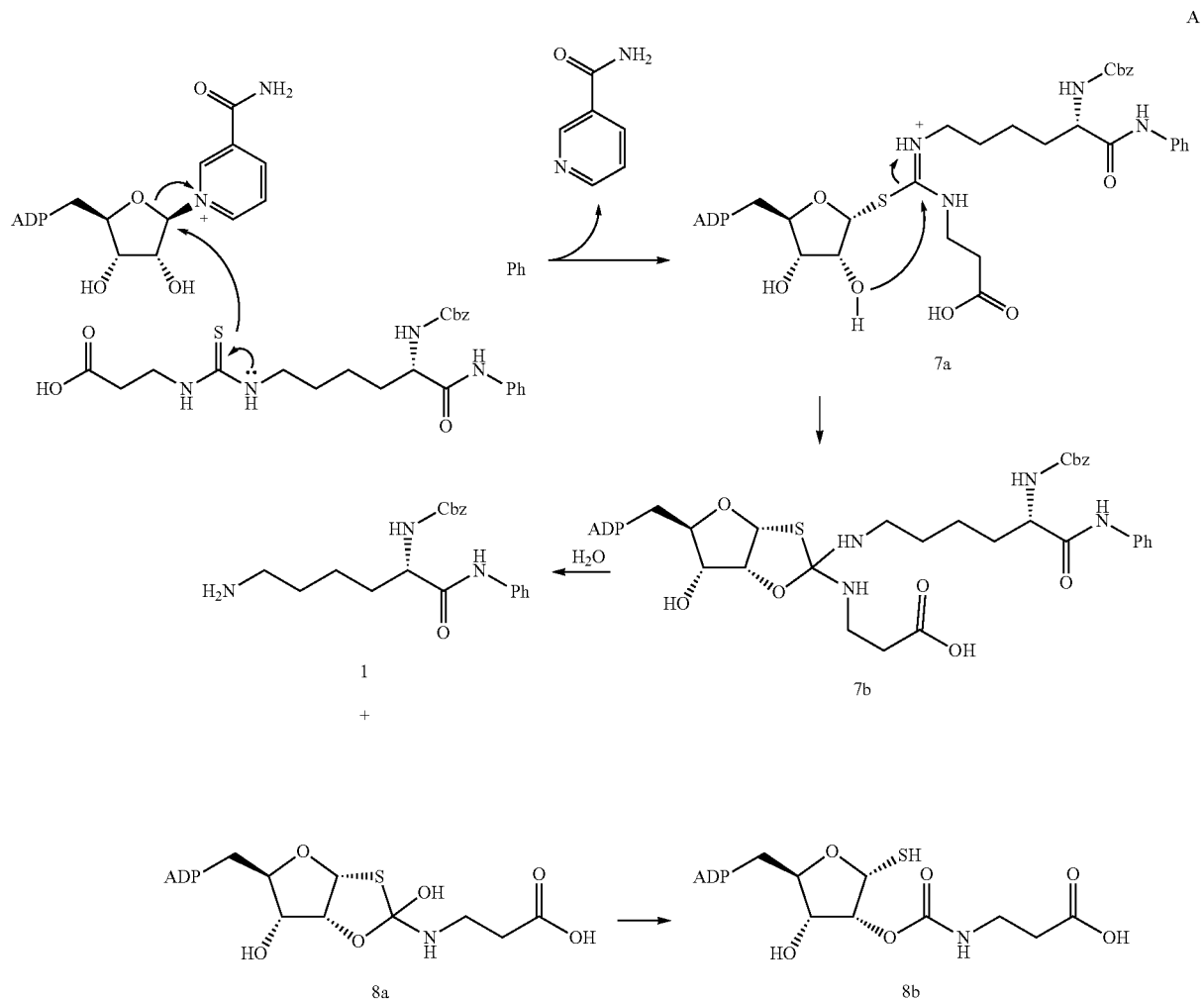

A

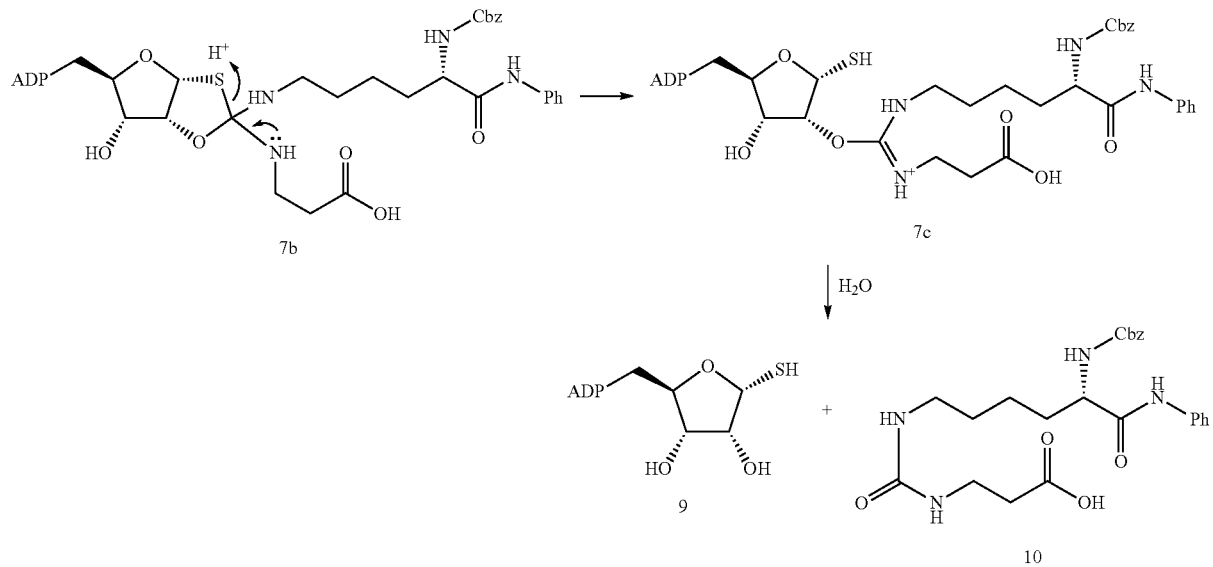

The intermediate Compound 7a, 7b, or 7c can be observed even after 5 hours of incubation. After 18 hours of incubation, Compound 5 was consumed and the intermediate 7a or 7b or 7c was almost gone. The major product detected in the reaction mixture was Compound 10, suggesting that the major decomposition pathway for 7a is pathway B. Together, these results support the idea that the thiourea Compound 5 is indeed a mechanism-based inhibitor of Sirt5.

Interestingly, the behavior of the thioglutaryl lysine Compound 3b is different from that of Compound 5. Using a similar LC-MS analysis, it was herein found that the covalent intermediate formed between Compound 3b and NAD, although detectable by MS, never accumulates to a significant amount based on the UV absorption on the LC. The foregoing results are likely responsible for Compound 3b being a less capable inhibitor of Sirt5 compared to Compound 5. After 18 hours of incubation with Sirt5 and NAD, an appreciable amount of Compound 3b was still left, suggesting that the formation of the covalent intermediate is slower. The decomposition of the covalent intermediate occurs mainly through the Sirt5-catalyzed deacylation pathway A as the major product detected is Compound 1 with an m/z of 356.33.

To summarize, thiourea Compound 5 forms a covalent intermediate with NAD in the presence of Sirt5. The intermediate (7a/7b/7c) is readily detected by LC. In contrast, the covalent intermediate formed between thioglutaryl lysine Compound 3b and NAD is hardly detectable by LC. The identities of the labeled peaks were confirmed by MS.

A further benefit of using the lysine-derived N,N'-disubstituted thiourea compounds described herein is that the synthesis is more convenient compared to the synthesis of thioacyl lysine derivatives. In particular, the same intermediate (Compound 4) can be easily converted to a variety of different thiourea compounds by reacting it with any of a variety of amines. Alternatively, Compound 1 can react with any of a variety of commercially available isothiocyanate compounds to synthesize a variety of lysine-derived thiourea compounds. These compounds can then be tested as inhibitors for different sirtuins. For example, Compound 4 was reacted with heptylamine to produce Compound 6, which is a Sirt2-specific inhibitor with an $IC_{50}$ value of 0.2 μM.

EXAMPLE 2

Synthesis and Investigation of Several Additional Sirt5 Inhibitors

The following additional compounds were investigated:

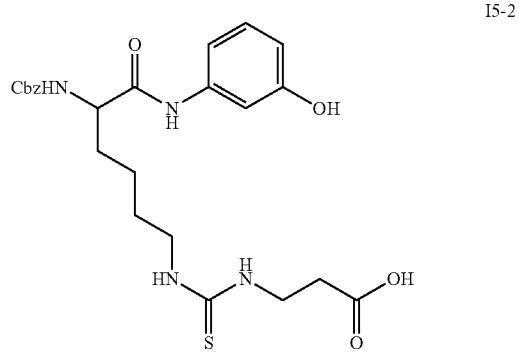 [SMILES: O=C(O)CCNC(=S)NCCCCC(NC(=O)OCc1ccccc1)C(=O)Nc1cccc(O)c1]

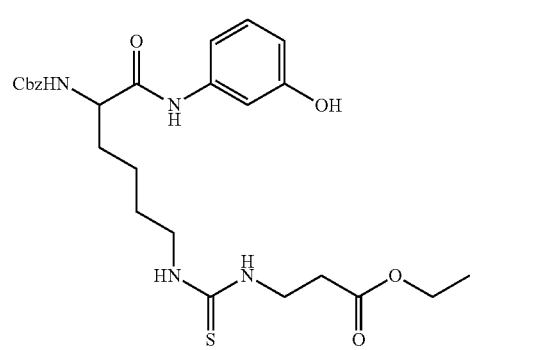

YC6-04
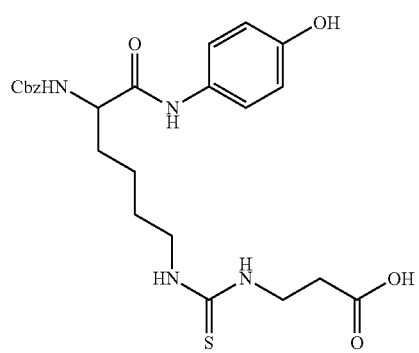
YC6-17
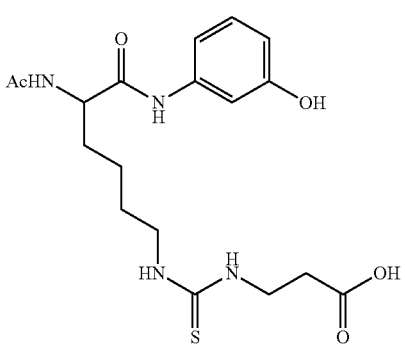
YC6-07
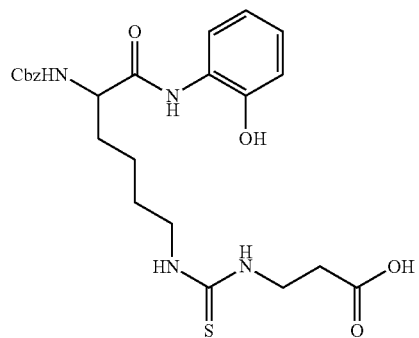
YC6-18
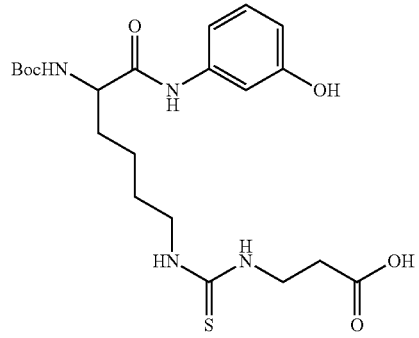
YC6-09
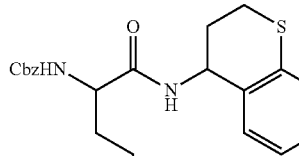
YC6-18e
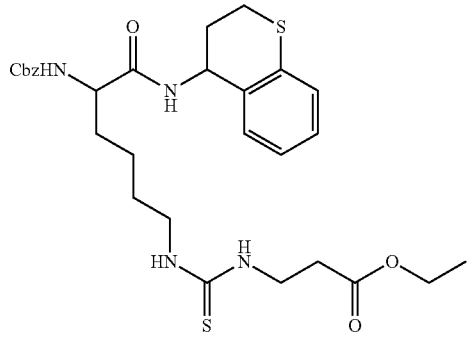
Two general exemplary synthetic methodologies for producing compounds shown above having an aminophenolic group at $R_4$ are as follows:
Method 1
YC6-14
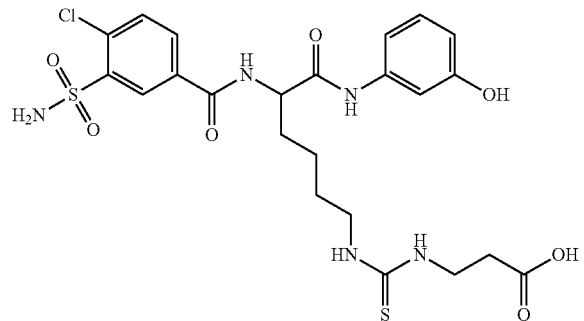
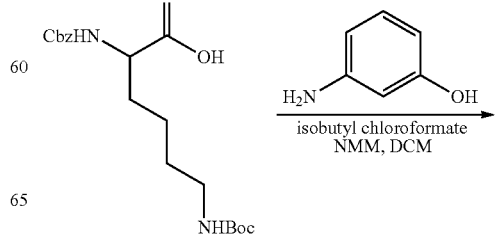

25
-continued
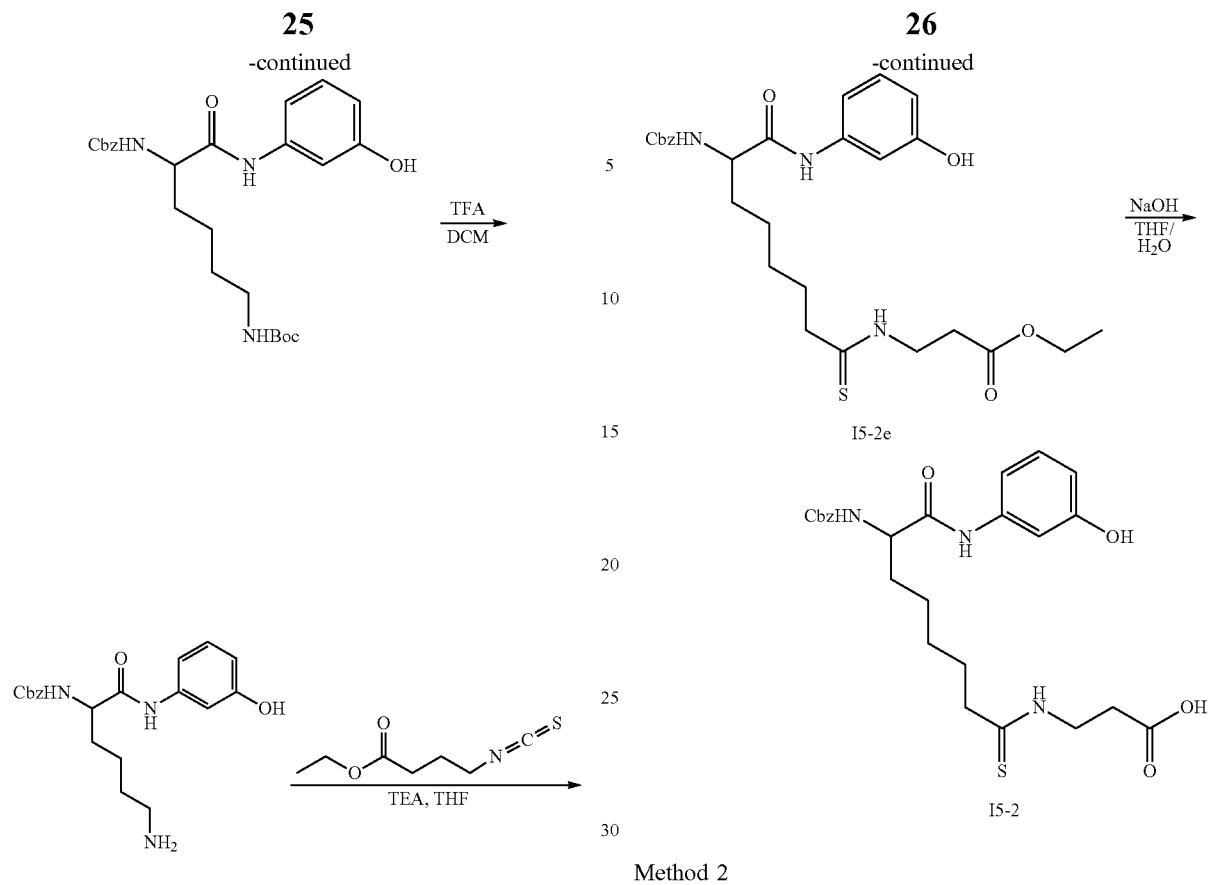
26
-continued
Method 2
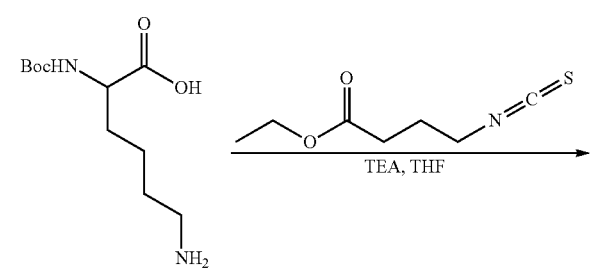
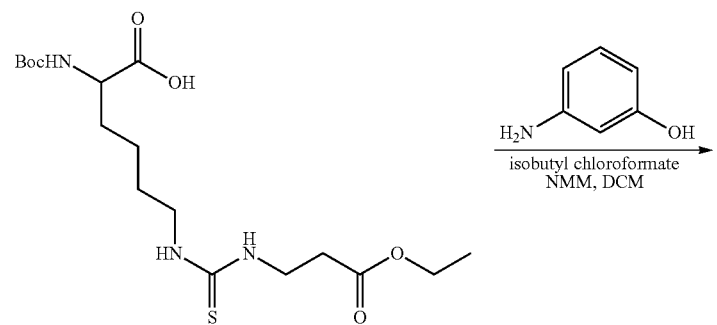

-continued

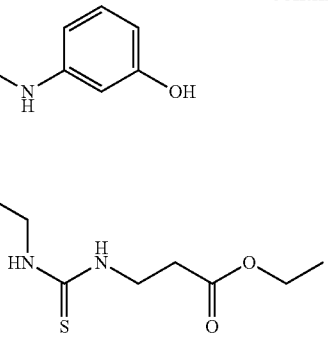

YC6-09e

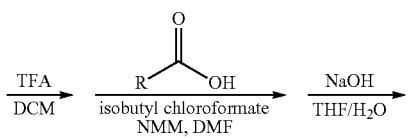

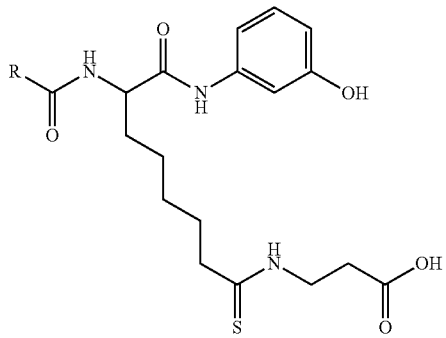

30

The compound 15-2e is the precursor that leads to compound 15-2. In cells, the ester bond in 15-2e should be easily hydrolyzed to produce 15-2. As compound 15-2e does not carry any negative charge, it should be cell permeable. The compound 15-2e may be used as a more permeable form (i.e., prodrug) for compound 15-2.

Reagents were obtained in the highest purity available and used as supplied. $^1$HNMR was performed on an INOVA 500 spectrometer. Solvents used in LCMS were water with 0.1% acetic acid and acetonitrile with 0.1% acetic acid. Analytic HPLC analysis was conducted by using Kinetex XB-C18 100A, 100 mm×4.60 mm, 2.6 μm reverse phase column with UV detection at 215 nm and 260 nm. Preparative HPLC purification was conducted using Targa™ Prep C18 10 μm 250×20 mm reverse phase column with UV detection at 215 nm and 260 nm.

Synthesis of Compound 1

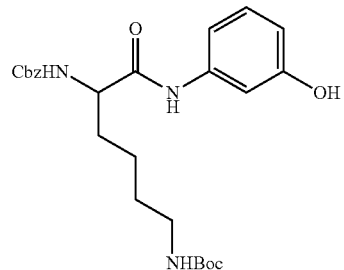

1

To a stirred solution of Nα-(carbobenzyloxy)-Nε-(tert-butoxycarbonyl)-L-lysine (380.4 mg, 1 mmol) and N-methylmorpholine (0.11 ml, 1 mmol) in dry dichloromethane (10 mL) was added iso-butylchloroformate (0.13 ml, 1 mmol) dropwise at 0° C., and the reaction mixture stirred at 0° C.

for 30 minutes. 3-aminophenol (131 mg, 1.2 mmol) was added at 0° C. and the reaction mixture was stirred overnight at room temperature. The solvent was removed under reduced pressure and the resulting residue was purified by flash chromatography on silica gel (DCM/MeOH=20:1) to afford the Compound 1 (438 mg, 93% yield).

Synthesis of Compound 15-2e

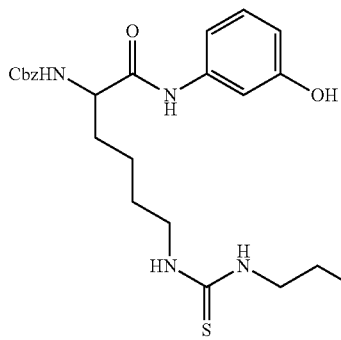

15-2e

Compound 1 (236 mg, 0.5 mmol) was treated with TFA (3 mL) and the mixture was stirred at room temperature for 1 hour. The solvent was removed under reduced pressure and the resulting residue was used in the next step without any further purification. To a stirred solution of the residue (234.2 mg, 0.5 mmol) and triethylamine (0.11 ml, 2.5 mmol) in dry dichloromethane (10 mL) was added dropwise 3-isothiocyanatopropionic acid ethyl ester (0.073 ml, 0.5 mmol). The reaction mixture was stirred overnight at room temperature. The solvent was removed under reduced pressure and the resulting residue was purified by flash chromatography on silica gel (DCM/MeOH=20:1) to afford the compound 15-2e (213 mg, 80.3% yield). $^1$H NMR (500 MHz, CDCl$_3$) δ9.06 (s, 1H), 8.05 (s, 1H), 7.38 (s, 1H), 7.33-7.17 (m, 5H), 7.06 (t, 1H, J=8.0 Hz), 6.90-6.58 (m, 4H), 6.19 (s, 1H), 5.12-4.95 (m, 2H), 4.42-4.37 (m, 1H), 4.09 (q, 2H, J=7.0 Hz), 3.76 (s, 2H), 3.26 (s, 2H), 2.60 (s, 2H), 1.87-1.55 (m, 2H), 1.50-1.27 (m, 4H), 1.20 (t, 3H, J=7.0 Hz). LCMS (ESI) calcd. for C26H35N4O6S ([M+H]+) 531.2, observed. 531.4.

Synthesis of Compound 15-2

I5-2

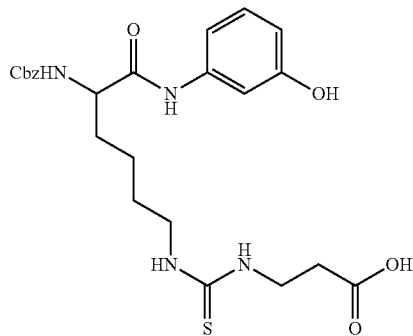

Compound I5-2e (53 mg, 0.1 mmol) was dissolved in THF:H$_2$O (1:1, 5 mL) and the mixture was cooled to 0° C. NaOH (6 mg, 0.15 mmol) was added and the reaction was allowed to warm to room temperature and stirred at room temperature (monitored by TLC). The reaction was acidified with 1 M aqueous HCl solution and extracted with DCM (3×20 mL) The combined organic layer was washed with saturated aqueous NaCl solution (20 mL), dried over anhydrous sodium sulfate, and concentrated in vacuo. Then the residue was purified by preparative HPLC to afford the compound 15-2 (20 mg, 40% yield) using a gradient of 0% solvent B for 10 minutes, 0% to 70% solvent B over 50 minutes, and 80% to 95% solvent B for 5 minutes. $^1$H NMR (500 MHz, CD$_3$OD) δ7.40-7.25 (m, 5H), 7.17 (t, 1H, J=2.0 Hz), 7.11 (t, 1H, J=2.0 Hz), 6.98-6.88 (m, 1H), 6.55 (dd, 1H, J=2.5 and 8.0 Hz), 5.18-5.02 (m, 2H), 4.26-4.15 (m, 1H), 3.18 (s, 2H), 3.46 (s, 2H), 2.60 (t, 2H, J=6.5 Hz), 1.90-1.70 (m, 2H), 1.67-1.55 (m, 2H), 1.55-1.37 (m, 2H). LCMS (ESI) calcd. for C$_{24}$H$_{31}$N$_4$O$_6$S ([M+H]$^+$) 503.2, observed. 503.4.

Synthesis of Compound

YC6-08

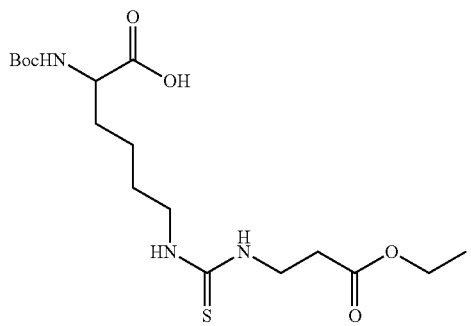

To a stirred solution of Nα-(tert-Butoxycarbonyl)-L-lysine (200 mg) in DMF (10.4 mL) at RT was added TEA (0.28 mL) and ethyl 3-isothiocyatopropionate (0.25 mL). After 16 hours, HCl was added until the pH of the reaction mixture was about 2. The mixture was extracted with EtOAc×3, washed with brine, dried over anhydrous Na$_2$SO$_4$, and concentrated under reduced pressure. The residue was subjected to flash column chromatography (CH$_2$Cl$_2$:MeOH=85:15) to give YC6-08 (300 mg) as a yellow oil.

Synthesis of Compound YC6-09e

YC6-09e

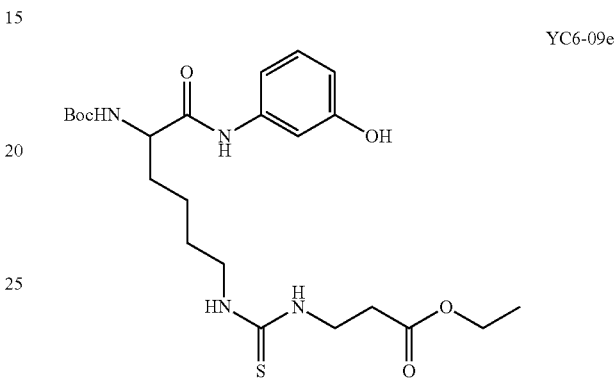

To a stirred solution of YC6-08 (300 mg) in CH$_2$Cl$_2$ at 0° C. in N-methylmorpholine (NMM) (0.13 mL), isobutyl chloroformate (0.16 mL) was added dropwise to the reaction mixture. After 20 minutes, 3-aminophenol (128 mg) was added to the solution. After 16 hours, was added CH$_2$Cl$_2$, washed with water and brine, dried over anhydrous Na$_2$SO$_4$, and concentrated under reduced pressure. The residue was subjected to flash column chromatography (hexane:EtOAc=2:3) to give YC6-09e (76 mg) as a yellow oil.

Synthesis of Compound YC6-09

YC6-09

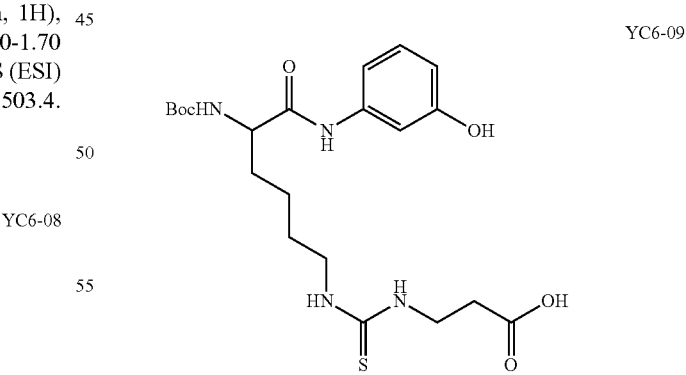

To a stirred solution of YC6-09e (20 mg) in THF (0.4 mL) at RT was added 1N NaOH (160 μL). After 16 hours, the THF was removed under reduced pressure. The mixture was then subjected to preparative RP-HPLC using a gradient of 35-50% CH$_3$CN (0.1% TFA) in water over 30 minutes to give YC6-09 as a white solid (7.7 mg, 41% yield).

Synthesis of Compound YC6-14

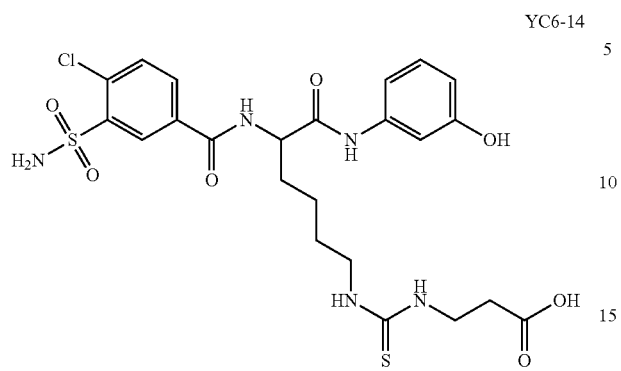

YC6-09e (110 mg) was dissolved in 1.1 mL TFA and 1.1 mL CH$_2$Cl$_2$ at RT. After stirring for 2 hours, the volatile material was removed under reduced pressure. To a stirred solution of residue (36 mg) in CH$_2$Cl$_2$ at 0° C. in N-methylmorpholine (NMM) (22 μL), isobutyl chloroformate (13 μL) was added dropwise to the reaction mixture. After 20 minutes, 4-chloro-3-sulfamoylbenzoic acid (21 mg) was added to the solution. After 16 hours, to the mixture was added CH$_2$Cl$_2$, and the mixture washed with water and brine, dried over anhydrous Na$_2$SO$_4$, and concentrated under reduced pressure. The residue was subjected to flash column chromatography (hexane:EtOAc=2:3) to give YC6-14e (200 mg) as a yellow oil. To a stirred solution of YC6-14e (15 mg) in THF (0.24 mL) at RT was added 1N NaOH (96 μL). After 16 hours, the THF was removed under reduced pressure. The mixture was then subjected to preparative RP-HPLC using a gradient of 36-46% CH$_3$CN (0.1% TFA) in water over 30 minutes to give YC6-14 as a white solid (12.6 mg, 88% yield).

Synthesis of Compound YC6-11

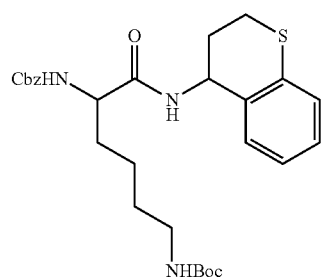

To a stirred solution of 1 (500 mg) in DMF (8.8 mL) at 0° C. in N-methylmorpholine (NMM) (0.18 mL), isobutyl chloroformate (0.22 mL) was added dropwise to the reaction mixture. After 20 minutes, thiochroman-4-ylamine (265 mg) was added to the solution. After 16 hours, to the mixture was added EtOAc, and the mixture washed with water and brine, dried over anhydrous Na$_2$SO$_4$, and concentrated under reduced pressure. The residue was subjected to flash column chromatography (hexane:EtOAc=2:1) to give YC6-11 (302 mg) as a white solid.

Synthesis of Compound YC6-18e

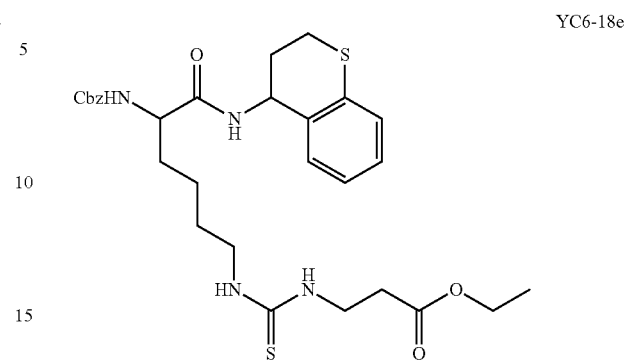

YC6-11 (152 mg) was dissolved in 0.14 mL TFA and 0.14 mL CH$_2$Cl$_2$ at RT. After stirring for 1 hour, the volatile material was removed under reduced pressure. To a stirred solution of 1 (220 mg) in THF (1.9 mL) at RT was added TEA (120 μL) and ethyl 3-isothiocyatopropionate (63 μL). After 16 hours, the THF was removed under reduced pressure. To the mixture was added EtOAc, and the mixture washed with water and brine, dried over anhydrous Na$_2$SO$_4$, and concentrated under reduced pressure. The residue was subjected to flash column chromatography (hexane:EtOAc=2:3) to give YC6-18e as a yellow oil (50 mg).

Synthesis of Compound YC6-18

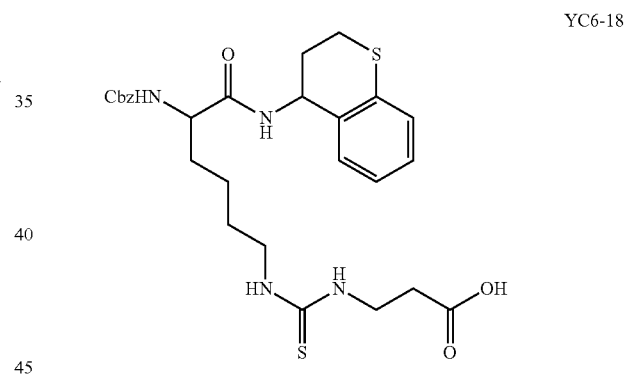

To a stirred solution of YC6-18e (23 mg) in THF (0.23 mL) at RT was added 1N NaOH (157 μL). After 4 hours, the THF was removed under reduced pressure. The mixture was then subjected to preparative RP-HPLC with a gradient of 0-95% CH$_3$CN (0.1% TFA) in water over 40 minutes to give YC6-18.

In Vitro SIRT5 Inhibition IC$_{50}$ Values

Table 2, below, summarizes the IC$_{50}$ results of the above-described SIRT5 inhibitors. As shown, two compounds, 15-2 and YC6-18, showed the most potent SIRT5 inhibiting results.

TABLE 2

Summary of IC$_{50}$ of SIRT5 inhibitors on different Sirtuins

|  | SIRT1 | SIRT2 | SIRT3 | SIRT5 | SIRT6 |
|---|---|---|---|---|---|
| I5 | NI | NI | NI | 12 | NI |
| I5-2e | 177.8 | 7.05 | NI | >200 (30%)[3] | NI[1] |
| I5-2 | NI | NI | NI | 0.89 | >200 (20%) |

TABLE 2-continued

Summary of IC$_{50}$ of SIRT5 inhibitors on different Sirtuins

|  | SIRT1 | SIRT2 | SIRT3 | SIRT5 | SIRT6 |
|---|---|---|---|---|---|
| YC6-04 | ND[2] | ND | ND | 3.28 | ND |
| YC6-07 | ND | ND | ND | 1.91 | ND |
| YC6-09 | ND | ND | ND | 4.37 | ND |
| YC6-14 | ND | ND | ND | 3.05 | ND |
| YC6-17 | ND | ND | ND | 13.6 | ND |
| YC6-18 | NI | NI | NI | 0.45 | ND |
| YC6-18e | ND | 3.92 | ND | >167 | ND |

[1]NI: no inhibition;
[2]ND: not determined;
[3]~20% inhibition at 200 µM

In Vivo SIRT5 Inhibition Assay

Because Compounds I5-2 and YC6-18 have a negative charge in their structures that can render them impermeable to cells, in most of the cellular studies, ester forms of these compounds (e.g., Compounds I5-2e and YC6-18e) were used. The ester forms are more cell-permeable, and once inside the cell, the ester bonds should be easily hydrolyzed by esterases to release the active SIRT5 inhibitors.

Figure 2A:
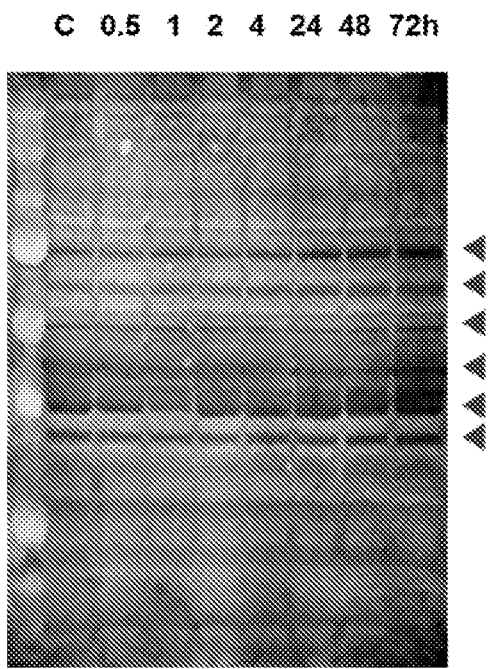
FIGS. 2A, 2B. Results of treatment of MCF-7 cell lines (control knock down) with 100 μM of the thiourea Compound I5-2e for different time points (0.5, 1, 2, 4, 24, 48, and 72 hours).
Figure 2B:
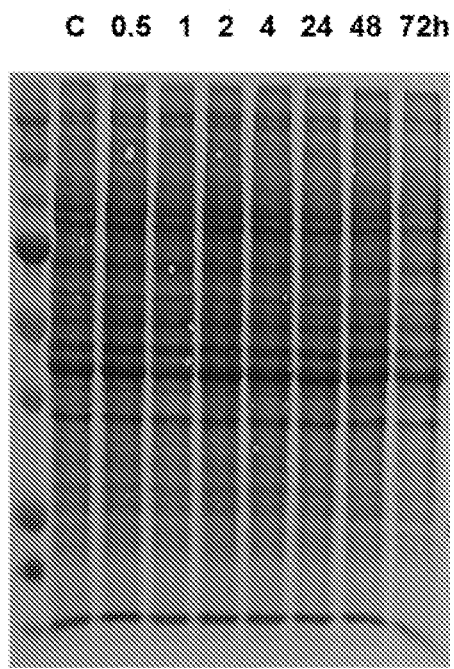

FIGS. 2A and 2B show the results of treatment of MCF-7 cell lines (control knock down) with 100 µM I5-2e for different time points (0.5, 1, 2, 4, 24, 48, and 72 hours). FIG. 2A is the Western blot image showing that treating the cells with Compound I5-2e increased the succinylation level on proteins at 48 and 72 hours. FIG. 2B is the Coomassie blue stained protein gel showing that each sample contains roughly the same amount of proteins. The control sample was treated with DMSO and grown for 72 hours. All the cells grew for the same duration. The results reveal that treatment with Compound I5-2e results in an increase in succinylation after 24 hours in MCF-7 cell lines.

Figure 3A:
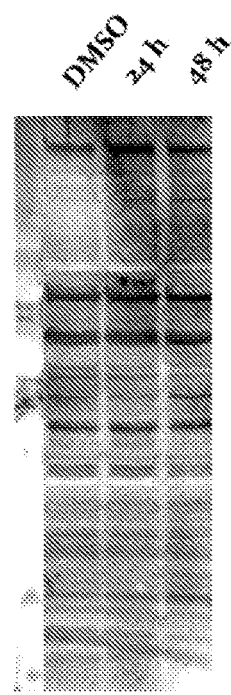
FIGS. 3A, 3B, 3C. Results of treatment of HeLa cell lines with 100 μM of the thiourea Compound YC6-18e at time points of 24 and 48 hours shown in FIGS. 3A and 3B.
Figure 3B:
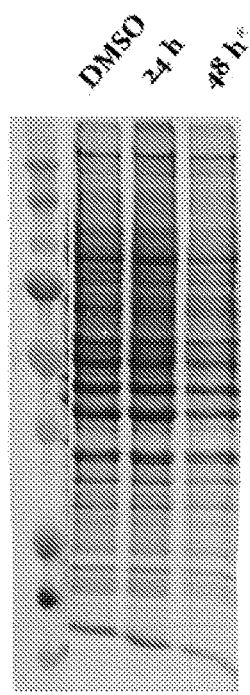
Figure 3C:
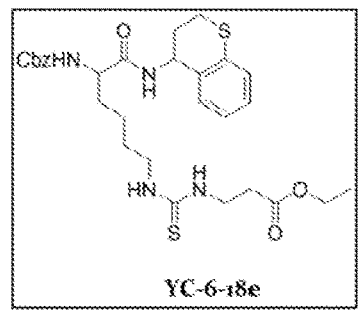

FIGS. 3A and 3B show the results of treatment of HeLa cell lines with 100 µM YC6-18e at time points of 24 and 48 hours, and FIG. 3C is the structure of YC6-18e. FIG. 3A is the Western blot image showing that treating the cells with Compound YC6-18e increased the succinylation level on proteins at 24 and 48 hours. FIG. 3B is the Coomassie blue stained protein gel showing that each sample contains roughly the same amount of proteins (the last lane has less protein, but the succinylation level shown in FIG. 3A is actually higher than other lanes, suggesting that the level of succinylation is increased after 48 hours of treatment with Compound YC6-18e). The results reveal that treatment with Compound YC6-18e can increase protein lysine succinylation. It was observed that the loading is lower for 48 hours but the succinylation intensity is slightly higher.

Figures 4A, 4B, 4C:
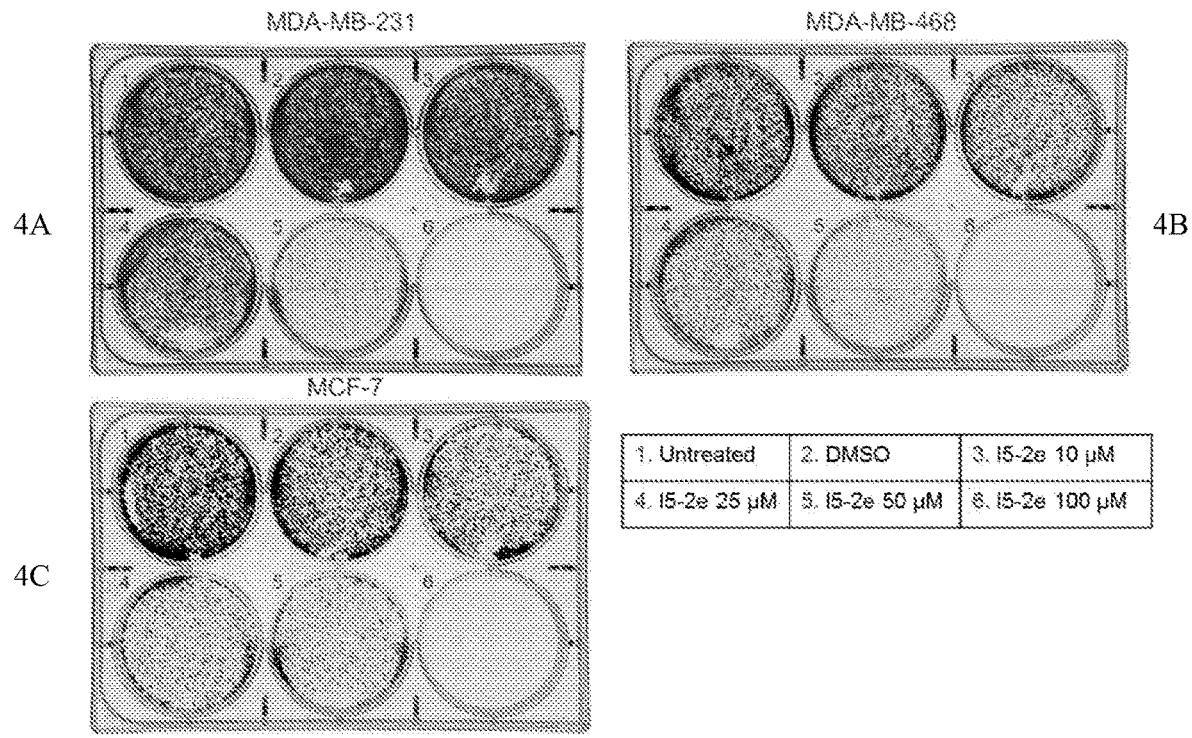
FIGS. 4A-4C. Results showing the dose-dependent effect of Compound I5-2e on foci formation in three human cancer cells designated as MDA-MB-231 (FIG. 4A), MDA-MB-468 (FIG. 4B), and MCF-7 cells (FIG. 4C). Each cancer cell line was assayed under the following six conditions: (1) untreated, (2) DMSO, (3) 15-2e at 10 μM, (4) 15-2e at 25 μM, (5) 15-2e at 50 μM, and (6) 15-2e at 100 μM.

Inhibition of Foci Formation of Human Cancer Cells by Prodrugs of Sirt5 Inhibitors FIGS. 4A-4C show the dose-dependent effect of Compound I5-2e on foci formation in three human cancer cells designated as MDA-MB-231 (FIG. 4A), MDA-MB-468 (FIG. 4B), and MCF-7 cells (FIG. 4C). Each cancer cell line was assayed under the following six conditions: (1) untreated, (2) DMSO, (3) 15-2e at 10 µM, (4) 15-2e at 25 µM, (5) 15-2e at 50 µM, and (6) 15-2e at 100 µM. The results demonstrate that Compound I5-2e is able to inhibit the foci formation of all three breast cancer cell lines starting at about 25 µM concentration.

Figures 5A, 5B:
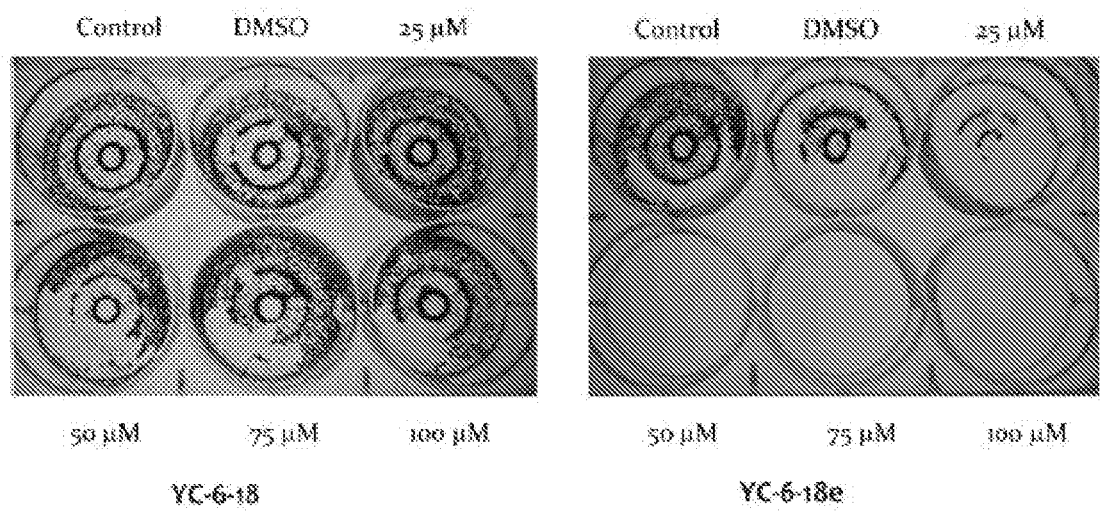
FIGS. 5A, 5B. Results of inhibition of MCF-7 cancer cells with Compound YC6-18 (FIG. 5A) and YC6-18e (FIG. 5B, ester prodrug form of YC6-18).

Inhibition of MCF-7 Cancer Cells by Compound YC6-18e 15,000 cells were seeded in each well and treated with 25, 50, 75, and 100 µM YC6-18 and YC6-18e. Media with the inhibitor/DMSO was changed every three days. Cells were stained with crystal violet after growing for 10 days. The results are shown in FIG. 5A (for YC-6-18) and FIG. 5B (for YC-6-18e). The results show that YC6-18e is unexpectedly very effective in killing MCF-7 at 25 µM concentration, whereas YC6-18 shows almost no effect due poor cell permeability.

While there have been shown and described what are at present considered the preferred embodiments of the invention, those skilled in the art may make various changes and modifications which remain within the scope of the invention defined by the appended claims.

What is claimed is:

1. A compound useful as a Sirt2 or Sirt5 inhibitor having the formula:

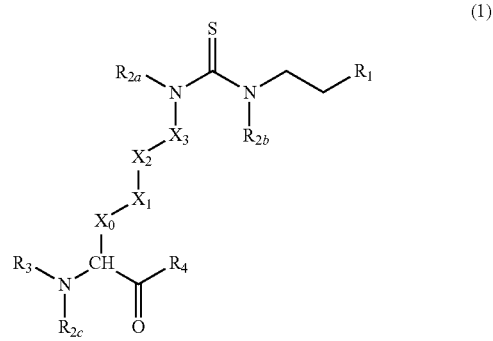

(1)

wherein:

R$_1$ is a carboxylate salt, carboxylic acid, carboxylic acid ester, or thiocarboxylate group;

R$_{2a}$, R$_{2b}$, and R$_{2c}$ are independently selected from hydrogen atom and methyl groups;

X$_0$, X$_1$, X$_2$, and X$_3$ are independently selected from —(CH$_2$)$_n$— and a bond, wherein n represents 1, 2, or 3, provided that at least one of X$_0$-X$_3$ is —(CH$_2$)$_n$—; and R$_3$ is selected from hydrocarbon groups containing 1-20 carbon atoms and optionally containing one or more heteroatoms selected from oxygen, nitrogen, sulfur, and halogen atoms; and R$_4$ comprises a cyclic hydrocarbon group optionally containing one or more heteroatoms selected from oxygen, nitrogen, sulfur, and halogen atoms.

2. The compound of claim 1, wherein R$_1$ is a carboxylate salt, carboxylic acid, or carboxylic acid ester group, wherein the ester group on said carboxylic acid ester is optionally a protecting group.

3. The compound of claim 1, wherein said compound has the following formula:

(1a)

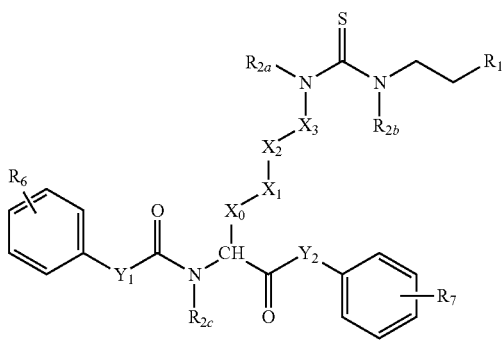

wherein:

$R_1$ is a carboxylate salt, carboxylic acid, carboxylic acid ester, or thiocarboxylate group;

$R_{2a}$, $R_{2b}$, and $R_2c$ are independently selected from hydrogen atom and methyl groups; $X_0$, $X_1$, $X_2$, and $X_3$ are independently selected from —(CH$_2$)— and a bond, wherein n represents 1, 2, or 3, provided that at least one of $X_0$-$X_3$ is —(CH$_2$);

$R_6$ and $R_7$ are independently selected from hydrogen atom, unsubstituted hydrocarbon groups having up to six carbon atoms, and heteroatom-containing groups;

$Y_1$ and $Y_2$ are independently selected from —O—, —NR$_5$—, —S—, —CH$_2$—, —CH$_2$O—, —CH$_2$NR$_5$—, and —CH$_2$S— groups; and $R_5$ is independently selected from hydrogen atom and methyl groups.

4. A pharmaceutical composition comprising a compound according to Formula (1) in claim 1 dispersed in a pharmaceutically acceptable carrier.

5. The compound of claim 1, wherein $X_0$, $X_1$, $X_2$, and $X_3$ are each —CH$_2$—.

6. The compound of claim 1, wherein $R_3$ comprises a protecting group.

7. The compound of claim 6, wherein the protecting group is selected from the group consisting of benzyloxycarbonyl (Cbz), p-methoxybenzylcarbonyl, t-butyloxycarbonyl (BOC), acetyl (Ac), benzoyl, and tosyl groups.

8. The compound of claim 1, wherein $R_4$ comprises a cyclic hydrocarbon.

9. The compound of claim 8, wherein said cyclic hydrocarbon is unsaturated.

10. The compound of claim 1, wherein $R_{2a}$, $R_{2b}$, and $R_{2c}$ are hydrogen atoms.

* * * * *